US008262554B2

(12) United States Patent
Sayeh et al.

(10) Patent No.: US 8,262,554 B2
(45) Date of Patent: Sep. 11, 2012

(54) APPARATUS AND METHOD FOR DETERMINING AN OPTIMIZED PATH TRAVERSAL FOR RADIATION TREATMENT DELIVERY SYSTEM

(75) Inventors: Sohail Sayeh, San Ramon, CA (US); Gopinath Kuduvalli, San Jose, CA (US); Daniel Brown, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1289 days.

(21) Appl. No.: 11/731,503

(22) Filed: Mar. 30, 2007

(65) Prior Publication Data

US 2008/0242969 A1 Oct. 2, 2008

(51) Int. Cl.
*A61N 5/10* (2006.01)

(52) U.S. Cl. .............................................. 600/1; 378/65

(58) Field of Classification Search .................. 600/1–8, 600/407; 378/65

See application file for complete search history.

(56) References Cited

U.S. PATENT DOCUMENTS 5,458,125 A 10/1995 Schweikard
6,741,674 B2 5/2004 Lee
7,266,176 B2 9/2007 Allison et al.
2005/0143965 A1 6/2005 Failla et al.
2007/0071168 A1 3/2007 Allison et al.

OTHER PUBLICATIONS

Coste-Manière, È., "Robotic whole body stereotacitc radiosurgery: clinical advantages of the CyberKnife® integrated system", The International Journal of Medical Robotics +Computer Assisted Sugery, 2005, www.roboticpublications.com, 14 pages.
International Search Report and Written Opinion of the International Searching Authority, PCT/US08/03896 filed Mar. 24, 2008, mailed Jun. 11, 2008, 16 pages.
Supplementary European Search Report for Application No. EP 08742245, mailed Jul. 1, 2010, 6 pages.
PCT International Preliminary Report on Patentability, PCT/US2008/003896 filed Mar. 24, 2008, mailed Oct. 15, 2009, 12 pages.
International Search Report and Written Opinion of the International Searching Authority mailed on Feb. 21, 2008, for PCT Patent Application No. PCT/US2006/36373, filed Sep. 18, 2006, 9 pages.

*Primary Examiner* — Charles A Marmor, II
*Assistant Examiner* — Carrie R Dorna
(74) *Attorney, Agent, or Firm* — Lowenstein Sandler PC

(57) ABSTRACT

An apparatus and method for determining optimized path traversal in a radiation delivery system is described. In one embodiment, determining an optimized path traversal in a radiation delivery system involves providing a plurality of spatial nodes used in a treatment plan, where each of the plurality of spatial nodes represents a position of a radiation source made available to the treatment plan for delivering radiation to a target, identifying a number of unused spatial nodes, from among the plurality of spatial nodes, at which radiation is not delivered according to the treatment plan, and skipping travel to one or more of the unused nodes by the radiation source when administering the treatment plan. Other embodiments are also described.

27 Claims, 14 Drawing Sheets

FIG. 3A
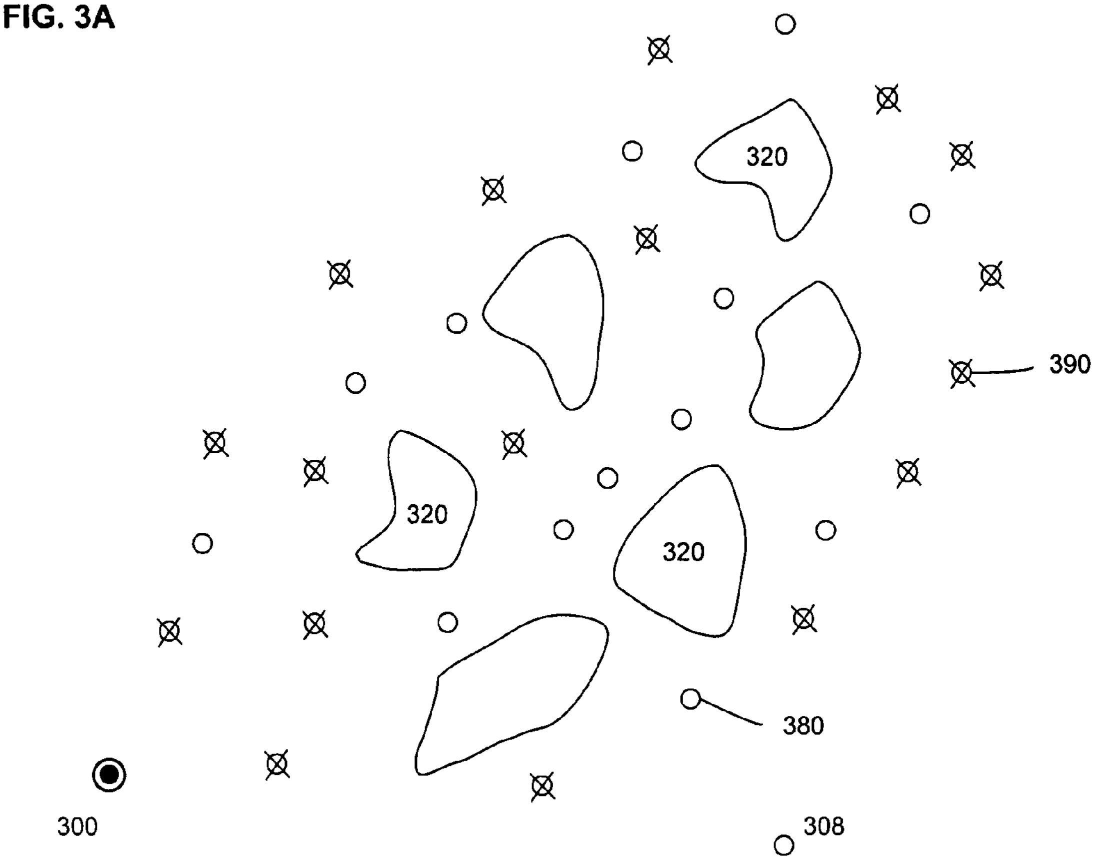
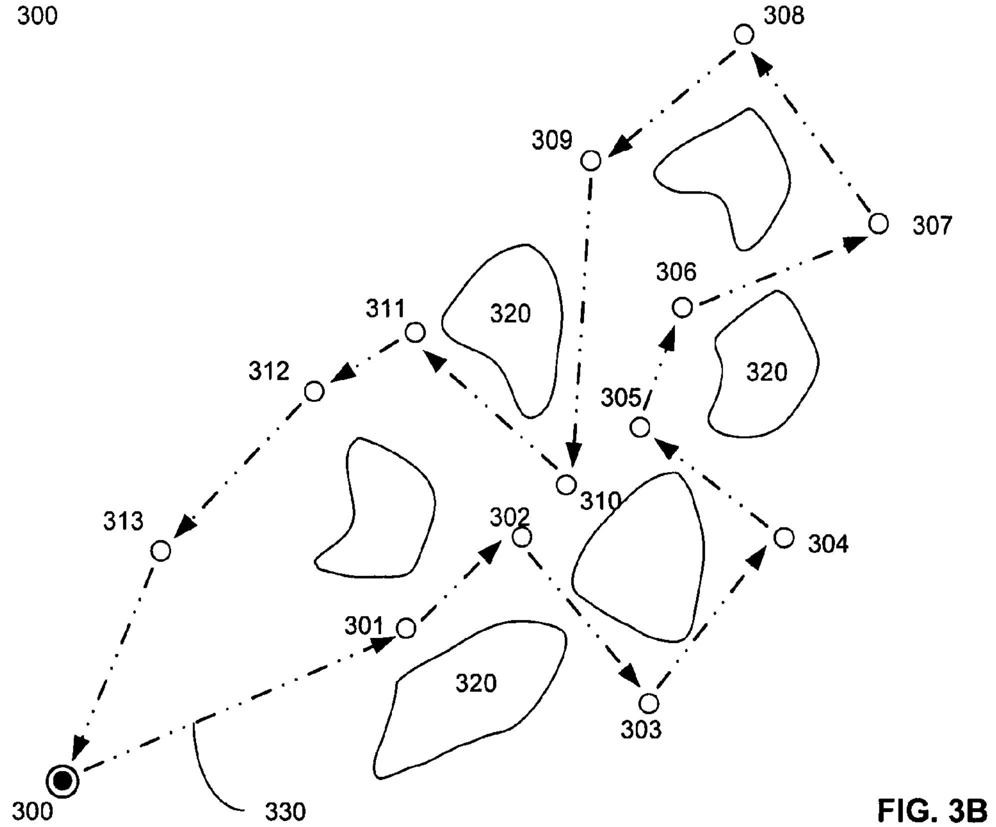
FIG. 3B

FIG. 5A
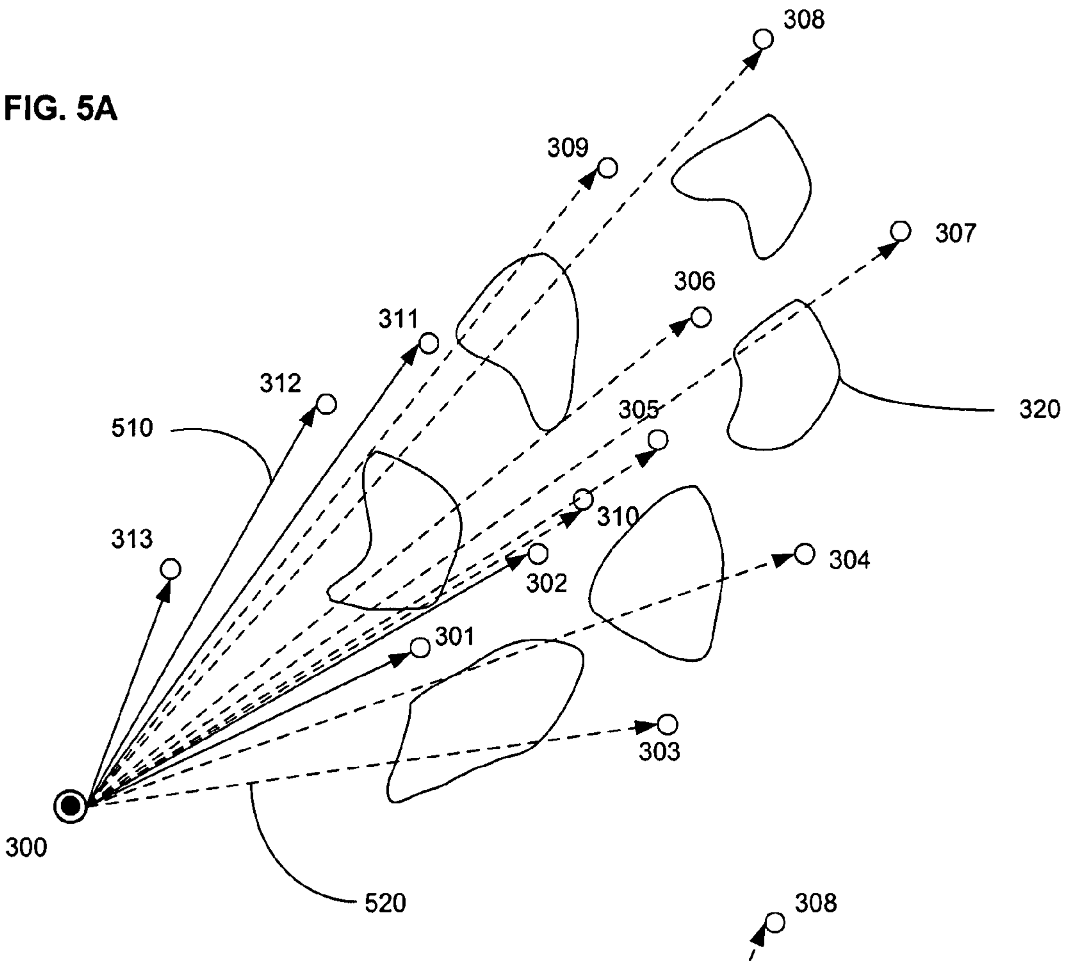
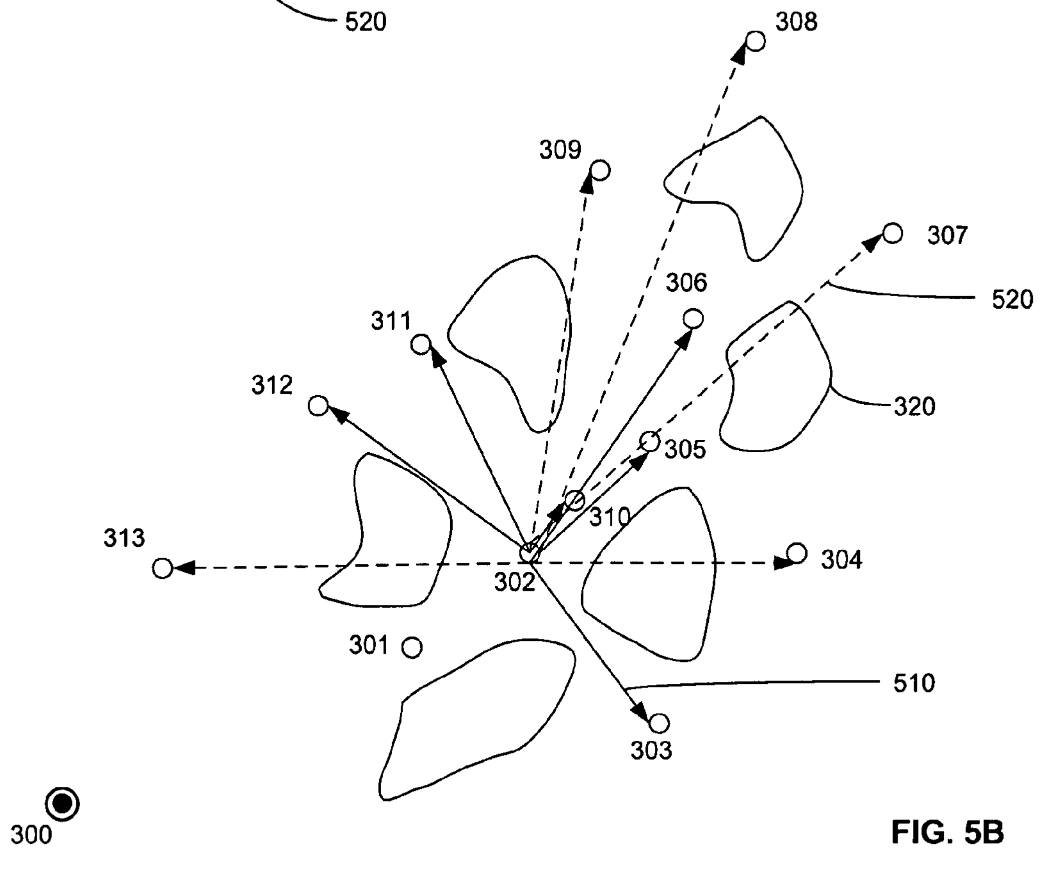
FIG. 5B

FIG. 5C
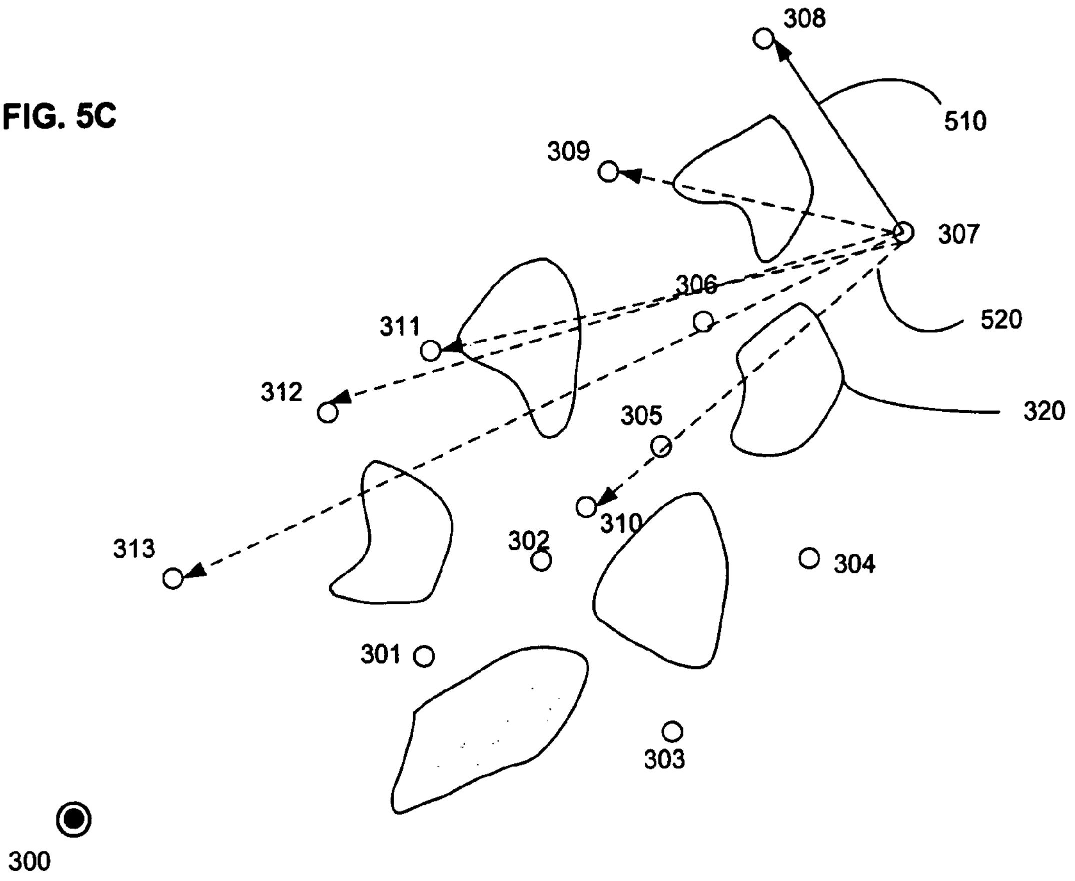
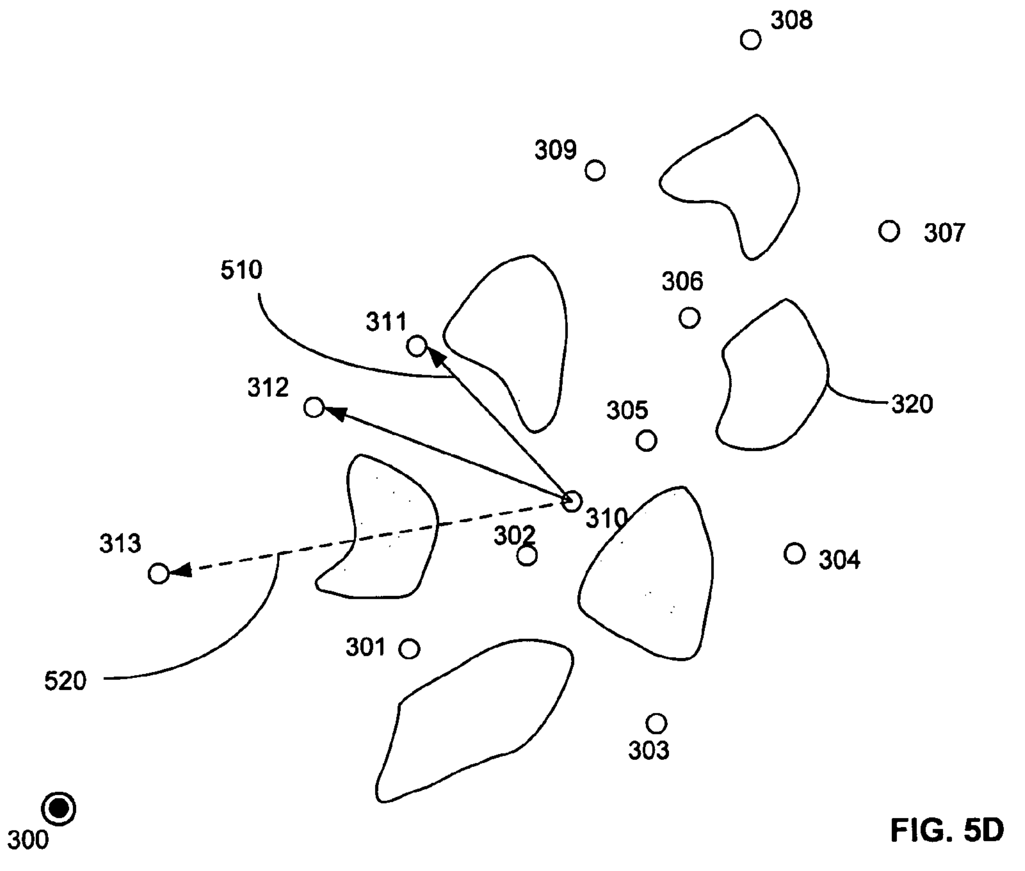
FIG. 5D

| | Home | 301 | 302 | 303 | 304 | 305 | 306 | 307 | 308 | 309 | 310 | 311 | 312 | 313 |
|---|---|---|---|---|---|---|---|---|---|---|---|---|---|---|
| Home | -- | O | O | X | X | X | X | X | X | X | X | O | O | O |
| 301 | -- | -- | O | X | X | O | O | X | X | X | O | X | X | O |
| 302 | -- | -- | -- | O | X | O | O | X | X | X | O | O | O | X |
| 303 | -- | -- | -- | -- | O | X | X | O | X | X | X | X | O | X |
| 304 | -- | -- | -- | -- | -- | O | X | O | X | X | X | X | X | X |
| 305 | -- | -- | -- | -- | -- | -- | O | X | X | O | O | X | X | X |
| 306 | -- | -- | -- | -- | -- | -- | -- | O | X | O | O | X | X | X |
| 307 | -- | -- | -- | -- | -- | -- | -- | -- | O | X | X | X | X | X |
| 308 | -- | -- | -- | -- | -- | -- | -- | -- | -- | O | X | O | O | O |
| 309 | -- | -- | -- | -- | -- | -- | -- | -- | -- | -- | O | O | O | O |
| 310 | -- | -- | -- | -- | -- | -- | -- | -- | -- | -- | -- | O | O | X |
| 311 | -- | -- | -- | -- | -- | -- | -- | -- | -- | -- | -- | -- | O | O |
| 312 | -- | -- | -- | -- | -- | -- | -- | -- | -- | -- | -- | -- | -- | O |
| 313 | -- | -- | -- | -- | -- | -- | -- | -- | -- | -- | -- | -- | -- | -- |

FIG. 6

FIG. 8A
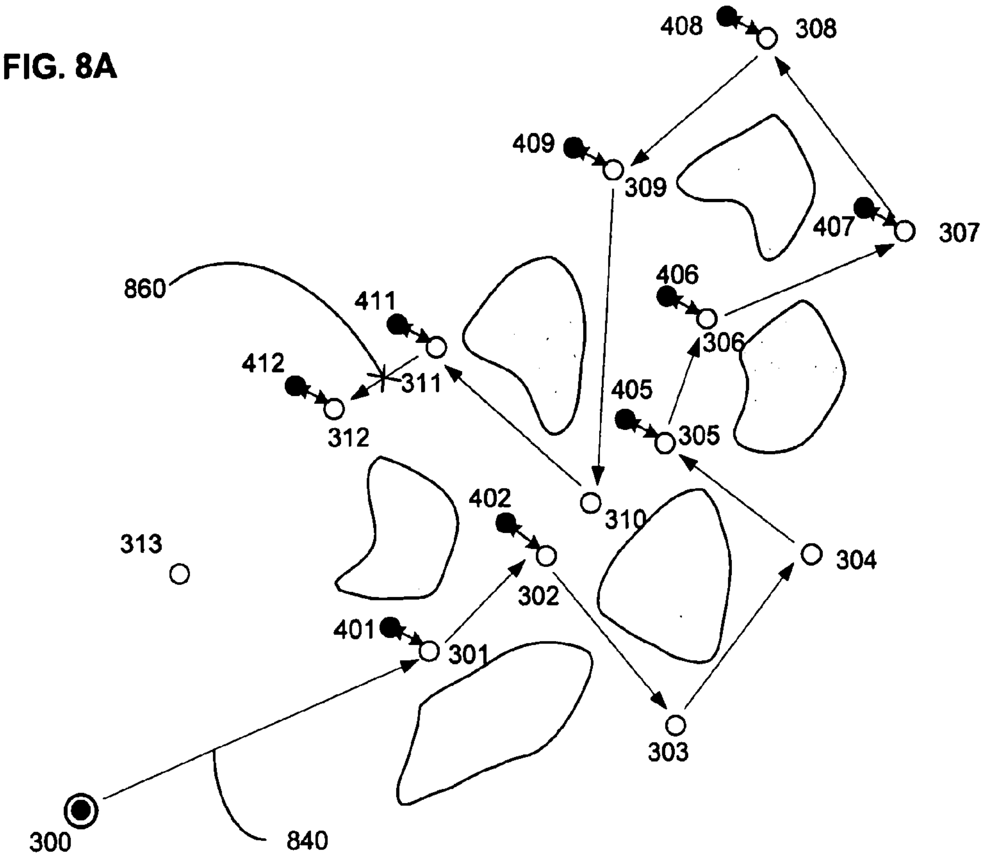
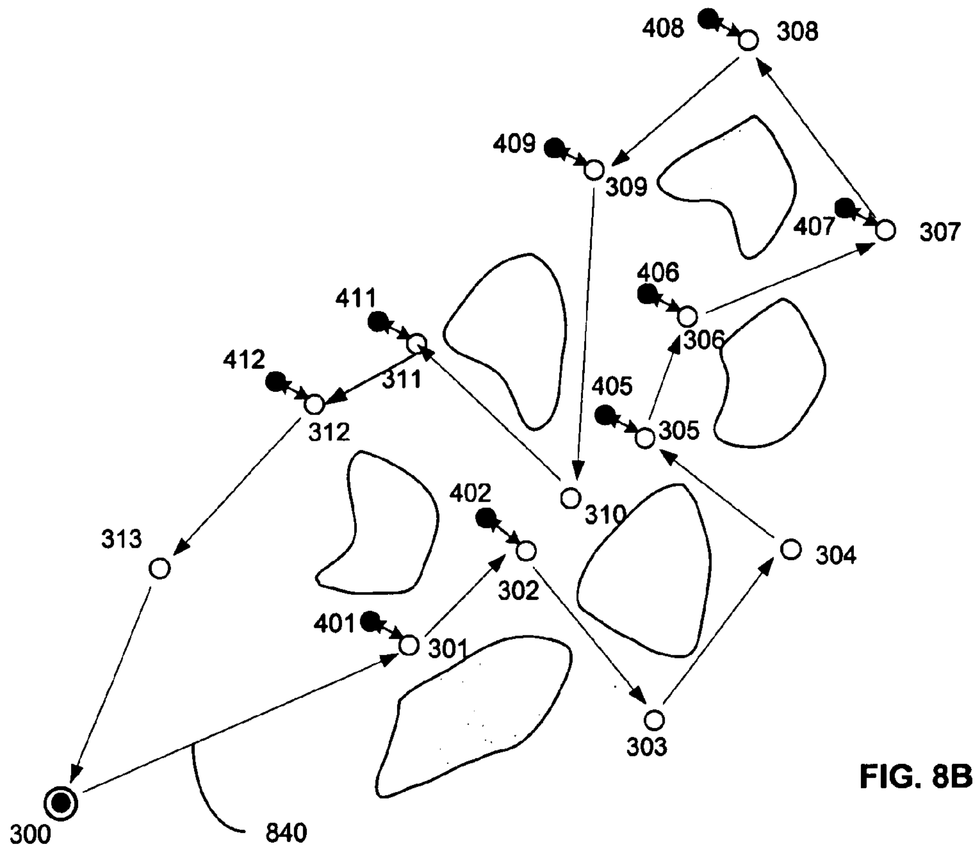
FIG. 8B

FIG. 9A
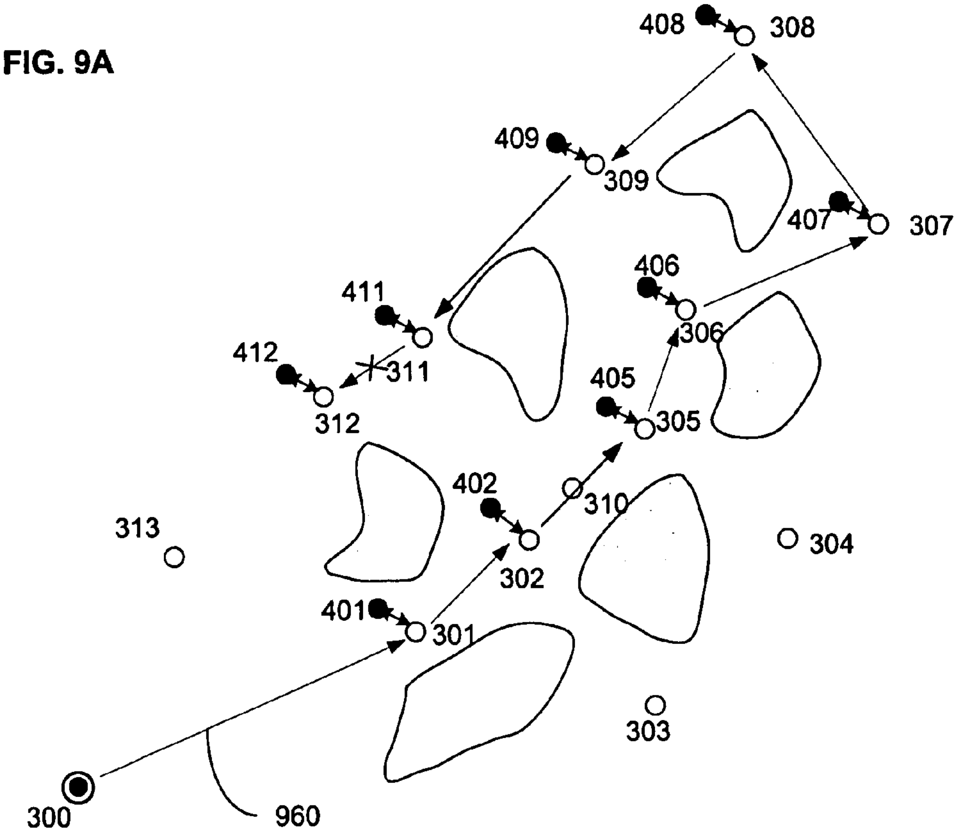
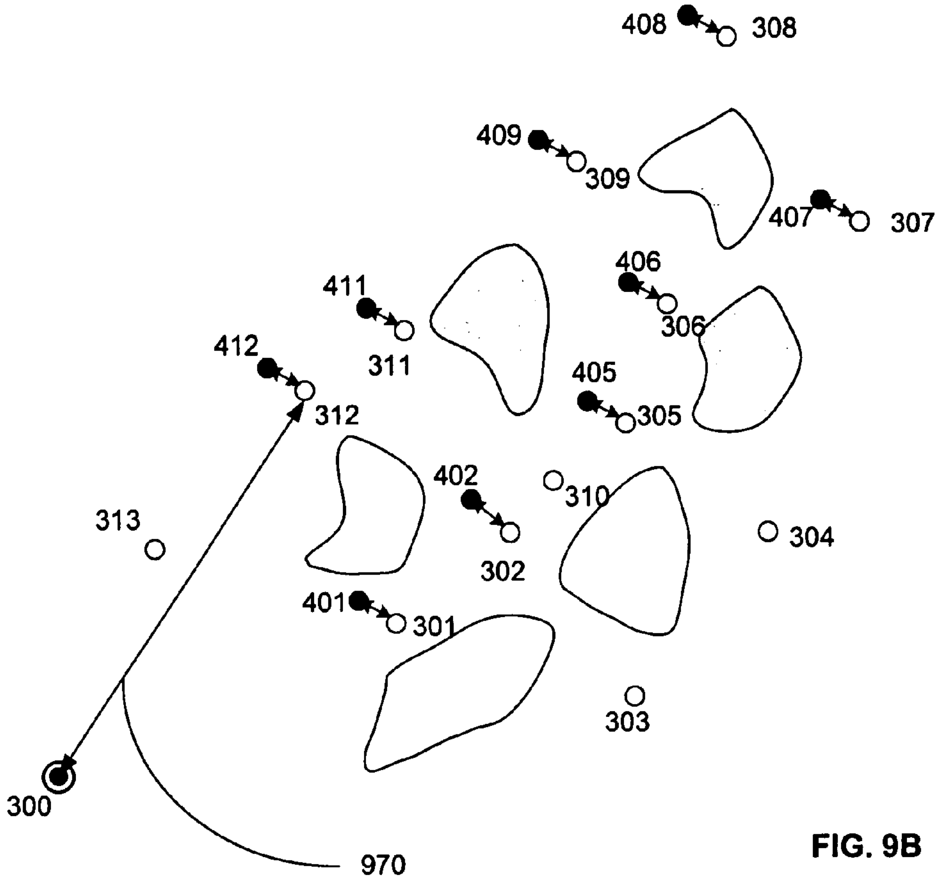
FIG. 9B

APPARATUS AND METHOD FOR DETERMINING AN OPTIMIZED PATH TRAVERSAL FOR RADIATION TREATMENT DELIVERY SYSTEM

TECHNICAL FIELD

This disclosure relates generally to the field of radiation treatment, and in particular but not exclusively, relates to determining an optimized path traversal for radiation delivery system.

BACKGROUND

Radiation treatment is referred to as a procedure in which radiation is applied to a target region or volume of interest (VOI) and is an inclusive term that includes both low dose treatments (e.g., radiotherapy) and high dose treatments (e.g., radiosurgery). Radiation treatments may require a high degree of precision and, thus, a system with components that can meet such requirements. One example of such system is the CyberKnife® system made by Accuray Incorporated of Sunnyvale, Calif. The CyberKnife® system is an image guided, robotic-based radiation treatment system. This system has a radiation source coupled to a robotic arm having multiple degrees of freedom that allows the radiation source to move and operate within a volume of space also referred to as a workspace. The multiple degrees of freedom allow the robot to conceivably achieve an infinite number of positional possibilities within its operating envelope. Allowing this type of movement provides flexibility but it may lead to other challenges. First, it creates a challenge for the treatment planning system by making it difficult to select beams for treatment. Secondly, it would allow the robot to travel anywhere within its workspace, but it must also recognize obstructions in which to avoid. These challenges are solved by creating specific paths that the robot must follow during treatment delivery.

The specific paths may be created by defining some specific workspace areas, for example, head and body. The workspace is generally a geometrical shape centered about a centroid of the geometrical shape which may be designed according to the location of the target. For example, the workspace can take the shape of a sphere or an ellipse. The workspace is generally defined by a source-to-axis distance (SAD), the distance between a collimator in a radiation source and the target. For example, in medical applications, a workspace for the anatomical head region may be defined by two spheres with SADs of approximately 650 mm and approximately 800 mm. In another example, a workspace for the neck may be defined by SADs ranging from about 650 mm to about 750 mm. This workspace is limited to the volume defined by the multiple concentric spheres with radii approximately ranging from about 650 mm to about 750 mm centering about the target in the neck region. When treating tumors in the rest of the body, the CyberKnife® system uses SAD values of approximately 900 to approximately 1000 mm. This approach compresses the workspace, but there are still an infinite number of positions where the robot could stop on the surfaces of these volumes. So, to address this, arbitrary positions are created along the surface of the sphere where the robot can stop to deliver treatments. Specifically, the workspace is characterized by a finite number of positions, referred to as spatial nodes, in the volume of space between the surface area of the smallest concentric sphere (650 mm) and the surface area of the largest concentric sphere (750 mm). These substantially uniformly distributed spatial nodes in a workspace are collectively known as the superset of nodes. However, only a partial number of this superset of nodes is used for radiation treatment with a particular CyberKnife® system that is installed at a site (e.g., hospital). Each site (e.g., hospital) at which a CyberKnife® system is installed may have a unique partial number of nodes that are defined by the geometry of the treatment room. A typical installation of a CyberKnife® system may have, for example, approximately 100 to approximately 130 of such nodes.

The partial number of nodes, within the superset of nodes, for a particular installation site provides a safe, or a collision-free, path of travel for the robotic arm mounted radiation source. This collision-free path of travel is obtained by arranging, in sequence, a partial number of nodes within the superset of nodes, so that the radiation source will not encounter any obstruction when traversing through the node sequence. This partial number of nodes within the superset of nodes is known as the template nodes. This safe and collision-free plan of travel is composed of direct paths between template nodes that are free of obstruction. The safe and collision-free path of travel is determined by a computation intensive off-line simulation and real-life testing in a CyberKnife® system treatment room. This safe and collision-free path of travel is formed from a pre-defined order or sequence of the template nodes and is unique to a treatment installation site or a particular treatment configuration.

Determination of the safe and collision-free plan of travel by a computer intensive off-line simulation process and testing with a real system is time consuming because of the large possibilities of safe or collision-free paths within a given superset of nodes and the arbitrary nature of the path selection process. An algorithm simulates a radiation source moving from a home position to a first spatial node, followed by a second spatial node, then a third, and a fourth etc., until an object or obstruction is encountered between spatial nodes. Upon encountering an obstruction, the algorithm eliminates that path by removing that destination spatial node, and applying the sequential number of that removed node to a next non-mapped spatial node. The simulation continues to reiterate and map spatial nodes to generate an obstruction free travel path that takes the radiation source back to the home position while eliminating spatial nodes that lead to collisions with obstructions or spatial nodes that are redundant. Ultimately a safe or collision-free path is established and determined by a set of spatial nodes. This set of spatial nodes is the template nodes, where each template node is numbered in sequence and if the radiation source follows the template nodes in order of the sequence, no obstruction will be encountered.

Each template node is assigned a number in the sequence so the radiation source travels along the path according to the order of the sequence. A treatment plan is generated from input parameters such as beam position and beam orientation that are available to the system based on the template nodes. The treatment plan specifies quantities such as the directions and intensities of the applied radiation beams, and the durations of the beam exposure. Treatment plans typically do not require delivery of the radiation beams at all of the available template nodes. However, due to the existing configuration of path traversal, even though the radiation source only needs to delivery radiation at a partial set of the template nodes, the radiation delivery source still has to visit all template nodes in an order defined by the sequence in the safe or collision-free plan of travel in order to ensure that the robotic arm mounted radiation source does not collide with the patient or another object. Having to cycle through the entire set of template nodes along a known safe or collision-free path increases the amount of time that is required to provide treatment.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIG. 3A is a 3-dimensional workspace mapped into a 2-dimensional map including a partial node set (template nodes) from the superset of spatial nodes, in accordance with an embodiment of the invention.

FIG. 3B is a 2-dimensional map with an outline of the safe or collision-free path of travel about the template nodes for the radiation source to deliver radiation treatments, in accordance with an embodiment of the invention.

FIG. 5A to 5D are different 2-dimensional maps illustrating direct path mapping of various example spatial nodes in determining a look up table for the optimal path traversal, in accordance with an embodiment of the invention.

FIG. 6 is an illustration of a look-up table containing results of the direct paths mapped among spatial nodes in a template of spatial nodes, in accordance with an embodiment of the invention.

FIG. 8A is a 2-dimensional map illustration of a radiation delivery source encountering an error between two spatial nodes while traveling on a safe or collision-free path formed by the template of nodes, in accordance with an embodiment of the invention.

FIG. 8B is a 2-dimensional map illustration of a modified new path of travel for the radiation delivery source after encountering the error occurrence, in accordance to an embodiment of the invention.

FIG. 9A is a 2-dimensional map illustration of a radiation delivery source encountering an error between two spatial nodes while traveling on an optimized safe or collision-free path formed by the subset of template nodes, in accordance with an embodiment of the invention.

FIG. 9B is a 2-dimensional map illustration of a new optimized safe or collision-free path for the radiation delivery source after encountering the error occurrence, in accordance to an embodiment of the invention.

DETAILED DESCRIPTION

Figure 1:
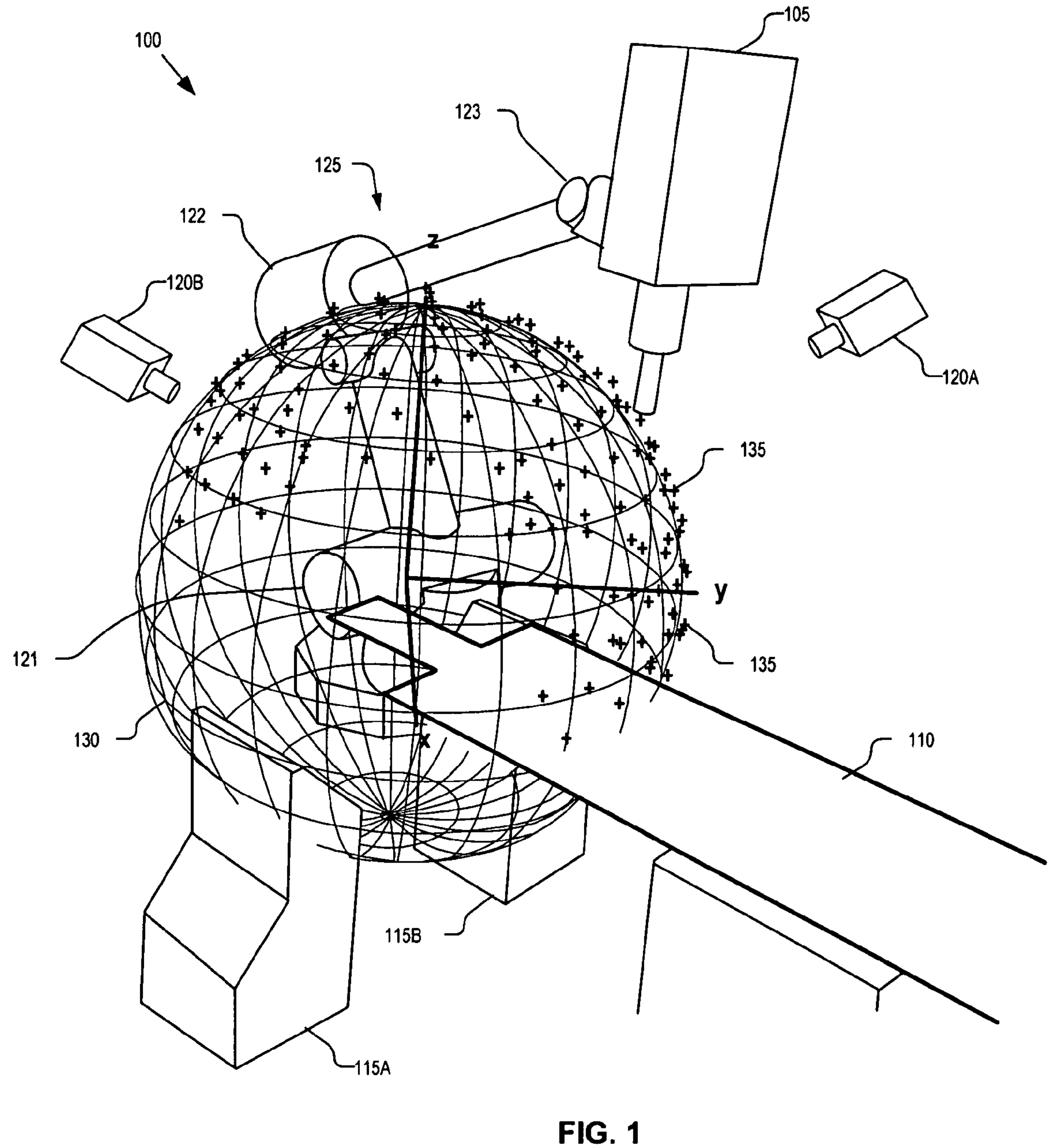
FIG. 1 is a perspective drawing illustrating a workspace of a radiation treatment delivery system including a plurality of spatial nodes at which to position the radiation source, in accordance with an embodiment of the invention.

Embodiments of a system and method for optimizing a workspace of a radiation treatment delivery system, for example, to reduce treatment times are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In one embodiment, the term "target" is used herein to refer to an anatomical feature(s) of a patient such as a pathological or normal anatomy, and may include one or more non-anatomical reference structures, at which a radiation source may target for radiation delivery. Although a specific type of target such as a pathological anatomy (such as a tumor, lesion, arteriovenous malformation, etc.) may be referred to below for ease of explanation purposes, the method and apparatus described herein may be applied to other types of targets. For example, the term "target" can be used to define a non-biological/non-human inanimate object or structure.

The term "safe" is defined herein as a description for travel of the radiation source following a path or a plan. "Safe" specifically refers to "collision-free" which also means that there is no obstruction. For example, when used to describe a path of travel or a plan of travel for a radiation source, "safe" means that there is no obstruction in the path of travel or the plan of travel and so the radiation source will travel collision-free along the path of travel or according to the plan of travel. In another example, when used to describe travel between two nodes, "safe" means that the direct path of travel for a radiation source between two nodes are collision-free, therefore, the nodes are safe nodes or collision-free nodes.

The term "radiation source" is defined as a linear accelerator that is used to deliver radiation to a target. In one embodiment, the "radiation source" is an X-band compact linear accelerator. The "radiation source" may also be interpreted to be a source that can be used to deliver radiation to a target. This "radiation source" is generally attached to a robotic arm so that the linear accelerator can travel to different positions in space where radiation treatments can be delivered to a target.

The method and apparatus for determining an optimized path of transversal for a radiation source discussed herein may be implemented using hardware, software, firmware or combinations thereof. The software modules discussed herein may be written in a variety of programming languages on which the software runs may be a Windows® OS from Microsoft Corporation of Washington or a Mac OS from Apple Computer of California. Alternatively, the OS may be a UNIX, Linux, or other operating systems (e.g., embedded or real-time operating system), etc. The software and OS may be run on any type of platform, for example, a personal computer (PC) platform, workstation, etc.

A software module, or computer program product, may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or other type of medium suitable for storing electronic instructions.

Unless stated otherwise as apparent from the following discussion, it will be appreciated that terms such as "identifying," "selecting," "determining," "generating," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

FIG. 1 is a perspective drawing illustrating a workspace of a radiation treatment delivery system including a superset of spatial nodes within a workspace to position the radiation source, in accordance with an embodiment of the invention. The illustrated embodiment of radiation treatment delivery system 100 includes a radiation source 105, and may also include, but not limited to, a treatment couch 110, detectors 115A and 115B (collectively 115, also referred to as imagers), imaging sources 120A and 120B (collectively 120), and a robotic arm 125.

Radiation treatment delivery system 100 may be used to perform radiation treatment (e.g., radiosurgery and/or radiotherapy) to treat or destroy a lesion (e.g., tumorous tissue) within a patient. Such a radiation delivery system has been described in "Robotic whole body stereotactic radiosurgery: Clinical advantages of the CyberKnife® integrated system" by Coste-Maniere et al. published in Int. J. Medical Robotics and Computer Assisted Surgery 2005;1 (2):28-39. During radiation treatment, in one embodiment of the radiation delivery system, the patient rests on treatment couch 110, which is maneuvered to position a volume of interest ("VOI") containing a target to a preset position or within an operating range accessible to radiation source 105 (e.g., field of view). In one embodiment, radiation treatment delivery system 100 is an image guided radiation treatment delivery system. Together, imaging sources 120 and detectors 115 act as an imaging guidance system to provide visual control over the position of treatment couch 110 and the patient thereon and the alignment of radiation source 105 with respect to the VOI within the patient. The imaging isocenter is defined by the intersection of radiation imaging beams that emit from the imaging sources to the imaging detectors. In an alternate embodiment, the imaging detectors 115 may exist in a different form than presented. For example, the detectors 115 may not be composed of two structures 115A and 115B, but instead, built into the ground or floor (not illustrated) to reduce the number of objects that may obstruct movement of the robotic arm. In another embodiment, treatment couch 110 may be coupled to a positioning system (not illustrated), such as a robotic arm, that receives feedback from the imaging guidance system to provide accurate control over both the displacement and orientation of the VOI within the patient relative to radiation source 105.

In one embodiment, the positioning system that is coupled to the treatment couch or the radiation source, such as a robotic arm 125, may have five or more degrees of freedom (DOF). For instance, this robotic arm may have five DOF that includes two rotational axes for translational movements along mutually orthogonal x-, and y- horizontal coordinate axes; and three rotational axes for roll-, pitch-, and yaw-rotational movements about x-, y-, and z- axes, respectively. The one (sixth DOF) substantially vertical, linear DOF includes a substantially linear axis for translation along a substantially vertical line in a z- coordinate axis perpendicular to the horizontal, x-, and y-coordinate axes. In another embodiment, the robotic arm 125 coupled to the treatment couch or the radiation source may have a different six DOF. The six DOF include three rotational axes for translational movements along mutually orthogonal x-, y-, and z- coordinate axes; and three rotational axes for roll-, pitch-, and yaw-rotational movements about the x-, y-, and z- axes respectively. The one substantially vertical linear DOF includes a substantial linear axis for translation along a substantially vertical line in a z-coordinate axis perpendicular to the horizontal x-, and y-coordinates axes.

In one embodiment, robotic arm 125 that is coupled to the radiation source 105 has five or more degrees of freedom (DOF) capable of positioning radiation source 105 with almost an infinite number of possibilities within its operating envelope. The robotic arm 125 has a shoulder assembly 121, an elbow assembly 122, and a wrist assembly 123. In one embodiment, the shoulder assembly 121 has two rotational DOF, the elbow assembly 122 has one rotational DOF, and the wrist assembly 123 has three rotational DOF. In this embodiment, the six degrees of rotational freedom produce a generous workspace for radiation source movements. Other embodiments with five or more DOF including but not limited to rotational or translational, or a combination of both types of movements are also possible.

FIG. 1 shows one embodiment of a workspace. Workspace can be of different geometrical shapes. In one exemplary embodiment, the workspace has a spherical geometrical shape 130 with its radius defined by a source-to-axis distance (SAD) from the centroid of the shape. SAD is the distance between the collimator in a radiation source and the target. The lone spherical geometrical shape 130 represents one of a series of concentric spheres, where each concentric sphere has a different radius specified by the different SAD centering about the centroid of the spheres. In one embodiment, one or a series of concentric spheres centering about the centroid collectively defines the workspace that is available for the radiation source to operate. In another embodiment, workspace may be one or a series of ellipses centering about the centroid of the ellipse. Multiple workspaces may be created and defined for different patient work areas. For example, different workspaces may be defined for different anatomies of a patient with each different workspace having a different SAD.

The spatial nodes 135 in FIG. 1, each represented by a "+" symbol (where only a few are labeled), collectively forms the superset of spatial nodes. The superset of spatial nodes defines spatial positions in the workspace at which the radiation source can physically occupy without interfering with any object or patient that may also be in the workspace. Spatial nodes 135 represent positions where radiation source 105 is allowed to stop and deliver a dose of radiation to the VOI within the patient. Spatial nodes 135 are substantially uniformly distributed over the surface of the workspace 130. In one embodiment of administering a treatment plan, the robotic arm 125 moves a radiation source 105 to each and every spatial node 135 following a predefined path. It should be appreciated that a treatment plan may call for the radiation source to visit a number of spatial nodes 135 more, same, or less than the number of superset nodes. In one embodiment, a treatment plan may call for the radiation source to visit one or more nodes more than once within a superset of nodes. In another embodiment, a treatment plan may call for the radiation source to visit a subset of nodes within a superset of nodes. Lastly, different treatment plans generally, but not always, specify different nodes because of the differences in target VOI, surrounding anatomical structures, and the clinical intent of the treatment plan.

While the superset of nodes are determined at time of installation or initialization of the radiation treatment delivery system 100, the template nodes used by a treatment plan is generally, but not always, determined at time of treatment planning. Template nodes are a subset of the superset of nodes and are defined in an ordered sequence. When a radiation source travels in space following the template nodes in an ordered sequence to delivery radiation treatments, the radiation source will follow a safe or collision-free path of travel and will not encounter any obstruction. In one embodiment of a treatment plan, a radiation source will visit each of the template nodes once and deliver radiation treatment at each of the template nodes once. In a different embodiment of a treatment plan, a radiation source will visit each of the template nodes once to ensure a safe or collision-free path of travel, but will deliver radiation treatment once each at only a selected partial number of the template nodes.

Figure 2A:
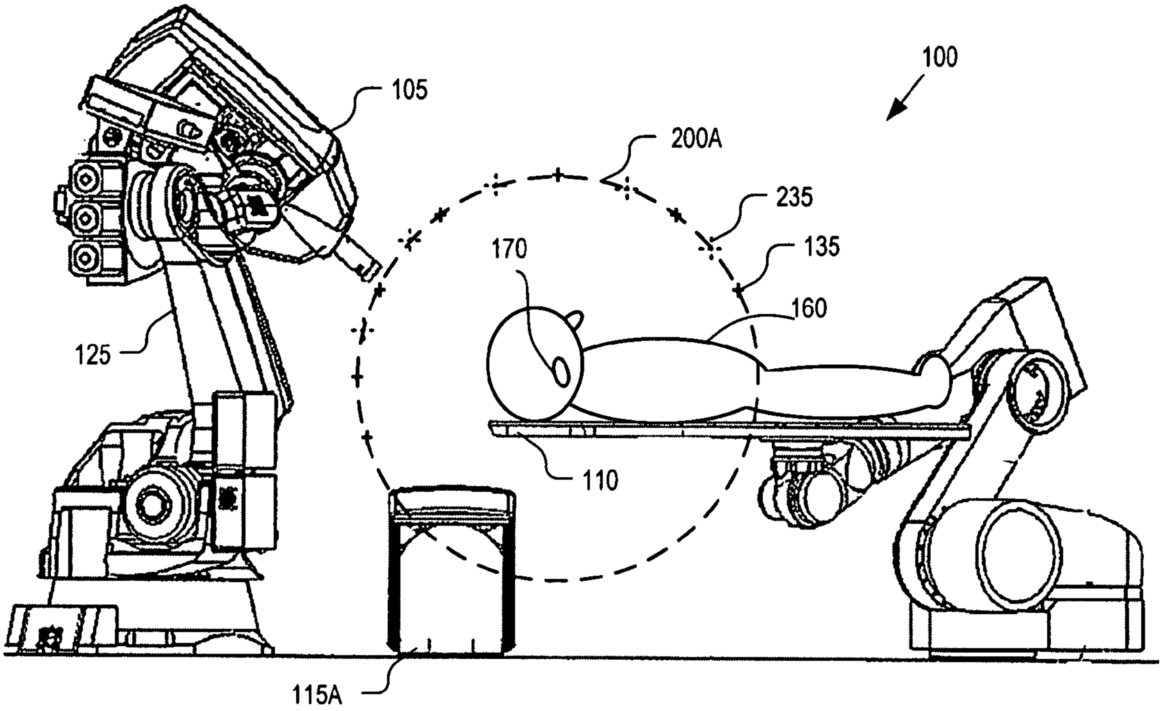
FIG. 2A is a side view illustrating a workspace of a radiation treatment delivery system including a partial node set (template nodes) from the superset of spatial nodes, in accordance with an embodiment of the invention.
Figure 2B:
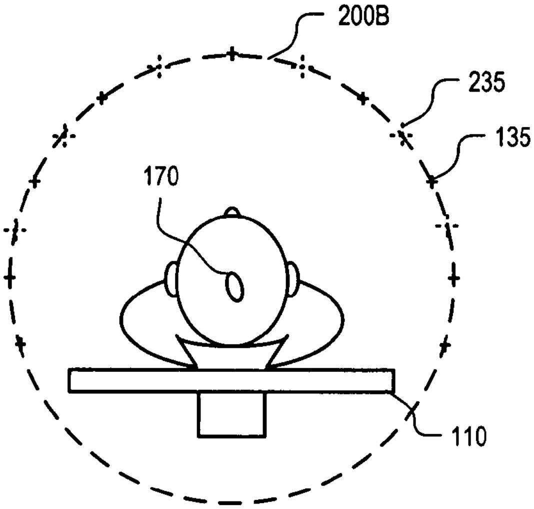
FIG. 2B is an end view illustrating a workspace of a radiation treatment delivery system including a partial node set (template nodes) from the superset of spatial nodes, in accordance with an embodiment of the invention.

FIG. 2A is a side view and FIG. 2B is an end view illustrating cross-sections 200A and 200B of workspace 130 including template nodes or a partial set of the superset of spatial nodes 135, in accordance with an embodiment of the invention. FIGS. 2A and 2B shows a patient 160 lying on a treatment couch 110 having a target or tumor 170, representing the centroid, from which SAD is measured in defining a workspace. As described, the spatial nodes 135 in FIG. 1 collectively represent spatial positions at which the radiation source can physically occupy in the workspace. Sections 200A and 200B illustrate some of those spatial nodes 135, evenly distributed about two different arcs on one of the concentric spheres having a SAD measured from the target 170. The spatial nodes 135 as shown are uniformly distributed and include the selected template nodes 235 having dashed "+" that are selected as part of a treatment plan. Therefore in one embodiment, template nodes 235 are used to generate a safe or collision-free path of travel and also where radiation treatments are delivered by the radiation source according to a treatment plan.

Template nodes and the superset of nodes may be represented in a 2-dimensional (2-D) configuration for easier understanding in a simpler illustration. FIG. 3A illustrates a 3-dimensional (3D) workspace mapped into a 2D map including the superset of nodes and the template nodes, in accordance with an embodiment of the invention. The map in FIG. 3A is an embodiment of a 2D equivalent of a useable 3D workspace. To allow for an easier understanding, the number of spatial nodes in this embodiment is simplified and reduced from the number of spatial nodes in some embodiments. Object 320 represents an object in 3D that is unfolded into 2D when the workspace in 3D is unfolded into 2D space. The spatial nodes represented by circles 380 and those represented by a circle with an "X" 390, collectively represents the superset of spatial nodes in a workspace. The spatial nodes represented by a circle with an "X", 390, are the spatial nodes not selected as template nodes. While many such unselected nodes are present, only one is labeled. The spatial nodes represented by circles 380 are the template nodes selected for a particular treatment plan. Each of these template nodes are equally represented by a circle 380 while each of the spatial nodes not selected as template nodes are equally represented by a circle with an "X" 390 in FIG. 3A. A home position 300 is the position where the radiation source starts and terminates. The home position 300 represents the resting position of the radiation source when the radiation source is not moving about to administer radiation treatments according to a radiation treatment plan.

In another embodiment, the template nodes 380 in FIG. 3A are ordered in a sequence to form a safe or collision-free path of travel for the radiation source. In the safe or collision-free path of travel, the radiation source moves from the home position to the lowest sequenced node and in order to the highest sequenced node according to the safe or collision-free path of travel, and moves from the highest sequenced back to the home position. FIG. 3B illustrates a 3-dimensional (3-D) workspace mapped into a 2-D map showing a safe or collision-free path of travel 330 as outlined by the template nodes, in accordance with an embodiment of the invention. One should appreciate that in one embodiment of a treatment plan, while a set of template nodes ordered in a sequence provides a safe or collision-free path of travel, radiation treatments do not have to be delivered at each template node. In one embodiment, a radiation source travels along the safe or collision-free path and visit all the template nodes and delivers radiation treatments at all the template nodes. In another embodiment, a radiation source travels along the safe or collision-free path and visit all the template nodes but delivers radiation treatments only at a partial number of the template nodes.

Delivery of radiation treatments at template nodes are determined by administration of treatment plans. Treatment planning determines at which of the template nodes the radiation source delivers radiation treatments. Although the treatment plan calls the radiation source to visit all the template nodes to ensure a safe or collision-free path of travel is maintained, a particular treatment plan may cause the radiation source to deliver radiation treatment only at a partial set of template nodes and not to the unused template nodes.

FIG. 3A differs from FIG. 3B in that template nodes in the former are identified while the template nodes in the latter are both identified and sequenced in a particular order to define a safe or collision-free path of travel. In another embodiment, treatment planning is completed such that the template nodes once identified from the superset of nodes are simultaneously sequenced. In other words, there are no separate steps in identification and sequencing where both are performed virtually simultaneously. As described in the background section, the template nodes are established when the system is installed at a site as determined by the geometry of the treatment room.

Figure 4A:
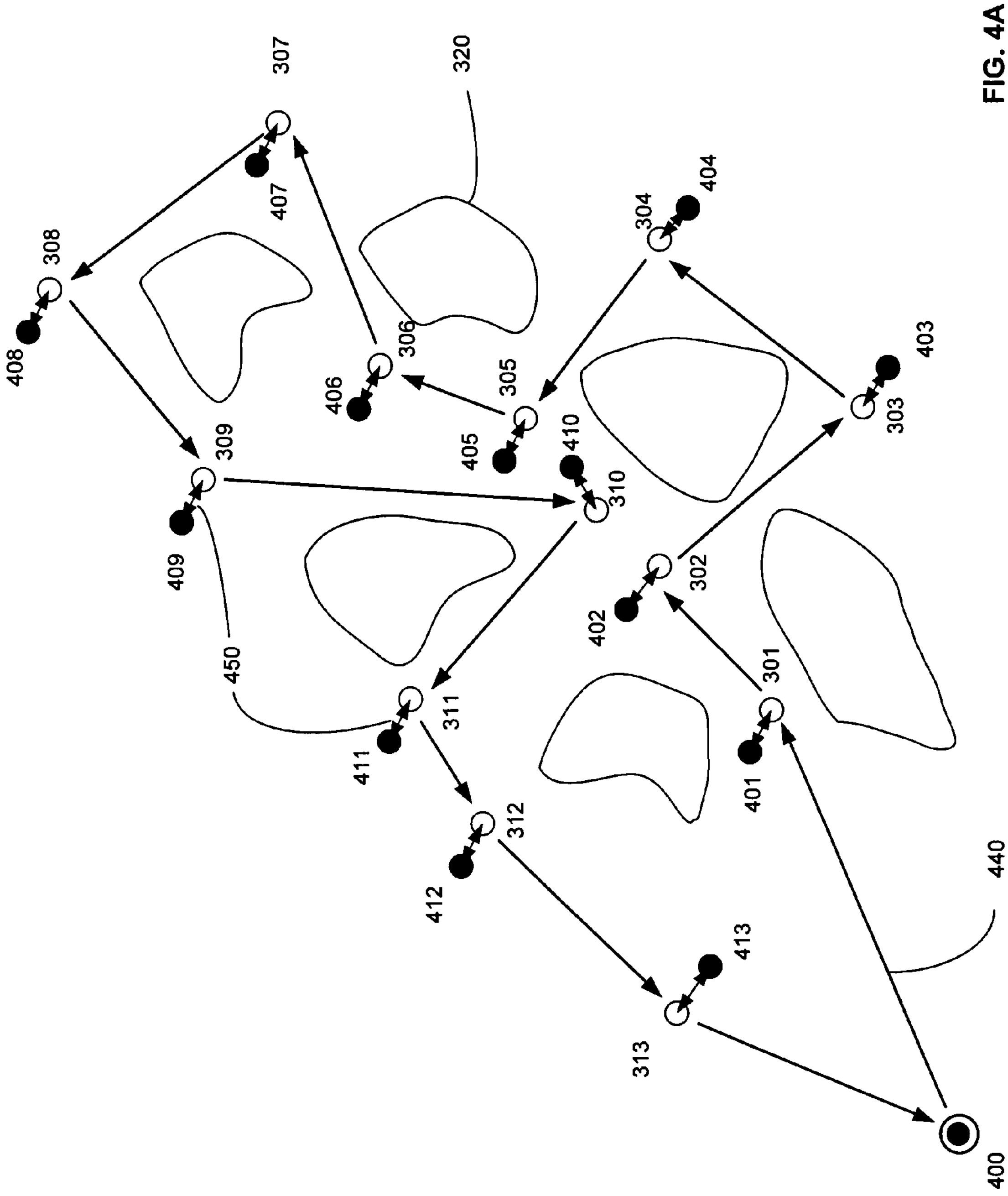
FIG. 4A is a 2-dimensional map with an outline of the safe or collision-free path for a radiation delivery source to administer radiation treatments at all the template spatial nodes, in accordance with an embodiment of the invention.

FIG. 4A is a 2-D map of the safe or collision-free path for a radiation source to deliver treatments at all the template nodes, in accordance with an embodiment of the invention. It should be appreciated that at this point, the template nodes are established and have been determined and setup by the process as described in the background section. The process described from this point forward should be distinguished from the template node setup process described in the background section. In one embodiment, the radiation source resides at the home position 400 at rest. On command to deliver radiation treatments, the radiation source follows the path 440 in direction of the arrows and travels to each of the template nodes 301-313 to deliver radiation treatment at each node. During the delivery of radiation treatment, while the radiation source is physically occupying the spatial position defined by a particular template node, the orientation of the radiation source varies (e.g., variations 450). In one embodiment, the radiation source has one or more orientation(s) during travel, for safety reasons, while having one or more different orientation(s), for delivering radiation treatments. For example, the collimator in the radiation source may be pointing away from the patient during travel between spatial nodes so any accidental firing of the radiation beam will not harm to the patient, but the collimator in the radiation source may be oriented in a particular angle towards the target during delivery of the radiation treatment. In one embodiment, the radiation source may have up to twelve (12) different orientations from which to select in delivering radiation treatments. The solid circles 401-413 represent the same spatial positions as each of the corresponding spatial nodes 301-313, but at one or more different orientation(s). In one embodiment, a radiation source arrives at a particular spatial node, for instance, node 305, at one orientation, but the radiation source re-directs to a new orientation 405 to deliver treatment, and then returning to a same or different orientation when arriving at the node before proceeding to the next node 306. In one embodiment, an original treatment plan as illustrated in FIG. 4A, radiation treatment is administered at each of the template nodes 301-313, and each of the template nodes 301-313 is visited in order of the sequence to ensure a path of travel that is safe from collision with any obstruction.

Figure 4B:
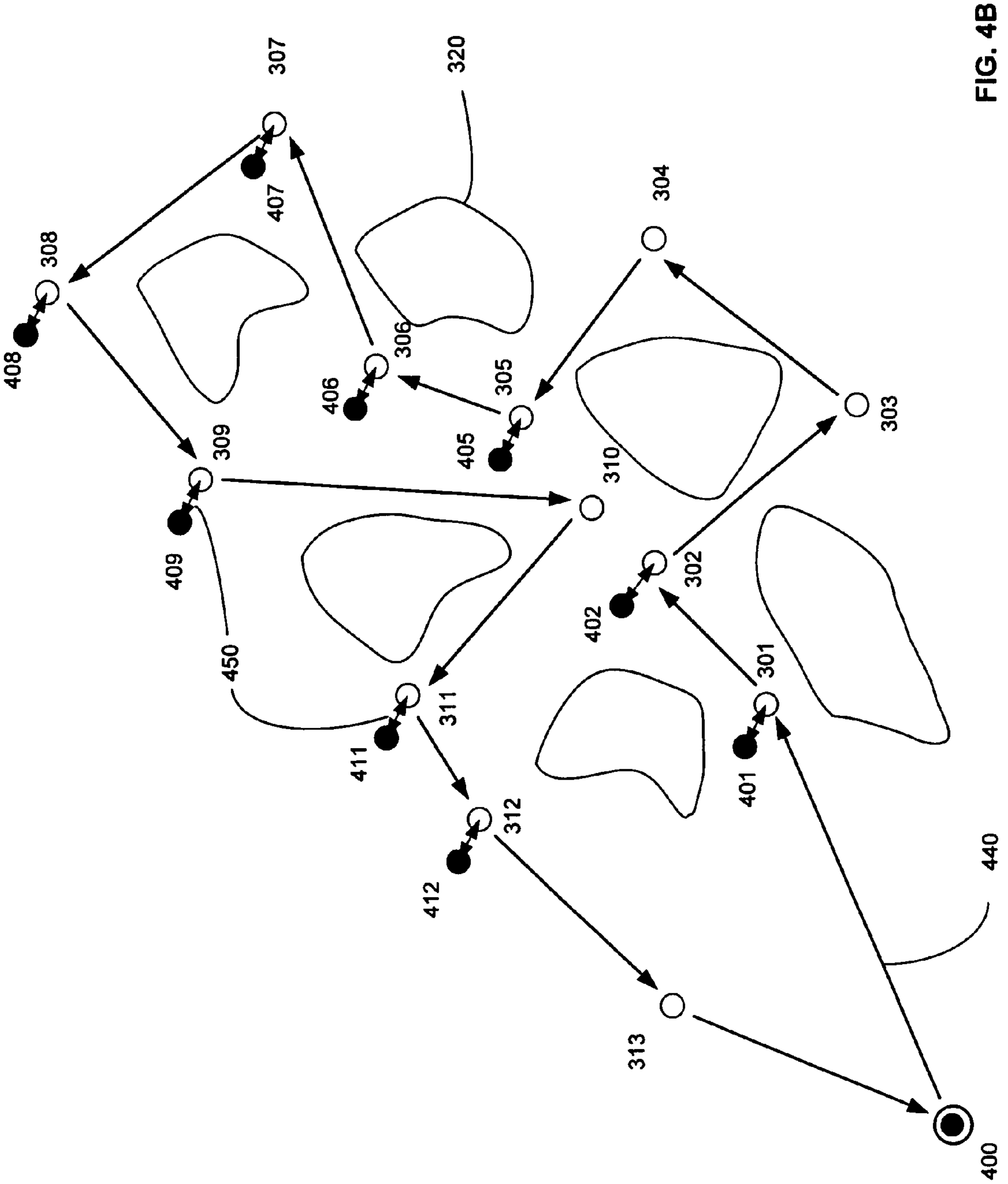
FIG. 4B is a 2-dimensional map with an outline of the safe or collision-free path for a radiation delivery source to administer radiation treatments at a partial set of the template spatial nodes, in accordance with an embodiment of the invention.

FIG. 4B illustrates a 2D map with an outline of the safe or collision-free path for a radiation source to travel and administer treatments at a partial set of the template nodes, in accordance with an embodiment of the invention. In one embodiment, as compared to an original treatment plan that calls for delivering radiation treatments at every template node (see FIG. 4A), a new treatment plan specifies radiation treatments are to be selectively delivered at a partial number of template nodes. FIG. 4B illustrates the new treatment plan using the same safe or collision-free path 440 going through all the template nodes 301-313 but delivering treatments at a selected partial set or subset of template nodes including 401-402, 405-409 and 411-412. In carrying out this new treatment plan, the radiation source travels from the home position 400 to each and every template node to follow the safe or collision-free path of travel. In other words, the radiation source travels and stops at each and every template node but only deliver radiation treatments at the selected template nodes. The safe or collision-free path 440 in the new treatment plan (FIG. 4B) is not altered as compared to the original treatment plan (FIG. 4A) and remains the same. The only difference is that in the new treatment plan the radiation source only stops at the selected template nodes to deliver treatment but not at the non-selected template nodes. While following the collision-free path 440 is safe, the overall distance of travel for the radiation source in the new treatment plan is the same as in the original treatment plan because the radiation source is forced to visit more nodes than necessary and, thus, extends overall treatment time. In one embodiment, a new method, such as direct path mapping, is developed to find an optimized path traversal for a new treatment plan where a partial set of template nodes are selected for delivering radiation treatments.

FIGS. 5A-5D are different 2D maps illustrating direct path mapping of various examples of spatial nodes in determining a reference table or database for an optimal path traversal for a new treatment plan, in accordance with an embodiment of the invention. FIGS. 5A-5D illustrate how safe or collision-free paths are determined for a new treatment plan where a partial set of template nodes is selected for delivering radiation treatments, as compared to an original treatment plan where radiation treatments are delivered at all the template nodes. Information about paths between spatial nodes is stored in a form for retrieval and access and may be implemented approximately before or during the time of execution of a treatment plan and/or approximately before or during the time of planning the treatment.

In one embodiment of direct path mapping, each template node is directly mapped to every other template node in the entire set of template nodes. The object is to identify if the direct path between any two template nodes contains an obstruction. When two nodes are connected by a direct path without an obstruction, each of the two nodes is known as a collision-free spatial node or collision-free node. Direct mapping is not like the identification and sequencing of template nodes for a plan of safe travel for the radiation source in an original treatment plan, where the template nodes are arbitrarily selected from the superset of nodes and arranged into sequence. On the contrary, direct mapping maps each of the template nodes already identified and sequenced in a systematic manner. Specifically, once the template nodes are identified and sequenced from the superset nodes, off-line simulation follows an algorithm where direct mapping is performed recursively from a spatial position to each of the other remaining spatial positions, one at a time, until each corresponding direct paths between all spatial positions represented by the home position and the template nodes are completed.

In one example, FIG. 5A is a 2D map illustrating all the direct paths from the home position to all the template nodes in space. An algorithm simulates movements of the radiation source from the home position directly to each template node in space. In this off-line simulation, each path will be identified as to whether the radiation source will collide with an obstacle or obstruction 320 such as the patient or another object in the workspace when traveling from one position to another. FIG. 5A shows collision-free paths 510 (solid arrows) from the home position to the corresponding spatial nodes 301, 302, 311-313 where there is no obstacle or obstruction 320. Thus, nodes 301, 302, 311-313 are collision-free spatial nodes or collision-free nodes to the home position. However, FIG. 5A shows obstacles or obstructions 320 in path(s) 520 (dashed arrows) from the home position to each of spatial nodes 303-310. While each of the arrows are only unidirectional, it should be understood that the object of direct mapping is to determine if a direct path of traversal between any two points, such as between the home position any one of the spatial nodes, has an obstruction or not. A collision-free path that has no obstruction suggests that the radiation source can move from home to that spatial node or vice versa and has no constraint in the direction of travel between the nodes. Similarly, a path containing an obstruction suggests the radiation source will not travel collision-free between the two points, in either direction. The direct mapping process is repeated for all template nodes.

In another example, FIG. 5B is a 2D map illustrating the direct paths from the spatial node 302 to other template nodes in space. FIG. 5B shows that if a radiation source is located at spatial node 302, the radiation source can reach spatial nodes 303, 305, 311 and 312 on collision-free paths 510 (solid arrows) that has no obstruction. These nodes, 303, 305, 311 and 312 are therefore collision-free spatial nodes or collision-free nodes to 302. However, the radiation source cannot reach spatial nodes 304, 307, 308, 309 and 313 because the direct paths 520 (dashed arrows) to those nodes will involve a collision with an obstacle or obstruction 320. Note that there is no path between template node 302 to home position or to template node 301. The algorithm performs direct path mapping systematically according to the sequential order of the template nodes. The algorithm will not re-map template nodes that have been previously mapped to reduce the overall time for mapping all spatial positions. When mapping template node 302 in FIG. 5B, the algorithm knows that direct mapping from home position (as illustrated in FIG. 5A) and from template node 301, two other nodes sequenced lower than template node 302, to the other template nodes have been completed. Since the path from home to template node to 302 was mapped (as illustrated in FIG. 5A) and the path from template node 301 to template node 302 was assume mapped (not illustrated), there is no need to revisit those template nodes.

FIG. 5C and FIG. 5D further illustrates this concept. FIG. 5C is a 2D map illustrating the direct paths from spatial node 307 to other remaining template nodes in space and FIG. 5D is a 2D map illustrating the direct paths from spatial node 310 to other remaining template nodes in space. In FIG. 5C paths are mapped from spatial node 307 to 308-313 respectively. While a direct path 510 (solid arrow) between spatial node 307 to spatial node 308 is collision-free, thus, nodes 307 and 308 are collision-free spatial nodes or collision-free nodes to each other. The remaining paths 520 (dashed arrows) between node 307 and nodes 309-313 suggest the radiation source will collide with obstacle or obstruction 320. Paths are not mapped from spatial node 307 to home position or to spatial nodes 301-306 because mapping to those template nodes are assume performed previously by direct mapping from each of those template nodes (not illustrated). Similarly, in FIG. 5D, paths are mapped from spatial node 310 to nodes 311 to 313. The direct paths 510 (solid arrows) from node 310 to 311 and 312, respectively, are collision-free, where 311 and 312 are collision-free nodes or collision-free nodes to 310, while the direct path 520 (dashed arrow) from node 310 to 313 results in the radiation source colliding with an obstacle or obstruction 320. Again, direct mapping from node 310 to the home position or to nodes 301-309 are not shown or performed because the information would have been previously obtained when direct mapping was performed for home and nodes 301-309 earlier (not illustrated).

In one embodiment, information generated from direct mapping is stored in a look-up table or database or in any format where the information can be accessed approximately at the time of treatment planning and/or approximately at the time of execution of the treatment plan. However, information may be stored in different formats or converted among different formats for convenient access or retrieval. For example, FIG. 6 illustrates the information generated from direct mapping of spatial nodes presented in FIG. 4A and 4B that are partially illustrated in FIG. 5A-5D and mapping of other spatial nodes not illustrated by FIG. 5A-5D. FIG. 6 presents the results of direct mapping of the home position and the thirteen spatial nodes 301-313 in a look-up table format. The left most vertical column represents the spatial position where a direct path originates, while the top most horizontal column represents the spatial positions where the direct path terminates.

Each of the remaining entries in the look-up table is marked with "--", "O", or "X". "--" indicates either a path is not applicable or mapping is not performed. For example, if the point of origin is 308 and the point of termination is 308, the path does not exist. Also, as described earlier by FIGS. 5A-5D, previously mapped paths are not repeated, therefore, as an example, if a direct path is mapped from an origin template node 302 to a terminal template node 304, there is no need to remap using template node 304 as an origin back to template node 302 because the result is the same and the process is redundant. "O" represents a collision-free path with no obstruction between two specified spatial nodes, in either direction. Thus each of the collision-free paths marked "O" also connects two collision-free spatial nodes or collision-free nodes. "X" represents a path containing an obstruction and prohibited for travel in either direction by the radiation source between the specified nodes, because taking that path will result in a collision with the obstruction. Note that the number of spatial nodes shown in FIG. 6 is reduced for the purpose of illustration. In some embodiments, the number of template nodes depends on the size of the workspace and resolution of spatial distribution of the spatial nodes over the workspace. For example, in one embodiment, the number of template nodes may easily range over 100.

In one embodiment, an object of the format used to store information is to allow retrieval or access of the information approximately at the time of planning a new treatment and/or approximately at the time of execution of a new treatment plan. Access or retrieval of the information without the need to convert the data into different formats allows faster calculation of alternate shorter safe paths for delivering radiation treatments according to a new treatment plan at partial set of in comparison to the original treatment plan where the safe or collision-free plan requires traveling to all template nodes in a defined order. In another embodiment, the information may be useful when the radiation source encounters an unforeseen error when traveling between two spatial nodes. Instead of starting again from the home position and traveling to all the spatial positions previously visited before the error occurrence, the information assists in quickly determining an alternate safe and shorter path of travel, skipping one or more of the template nodes previously visited, to complete the remaining treatment plan as originally intended. The applications and benefits derived from direct mapping in determining an optimized path traversal are illustrated in the following figures and tables.

Figure 7:
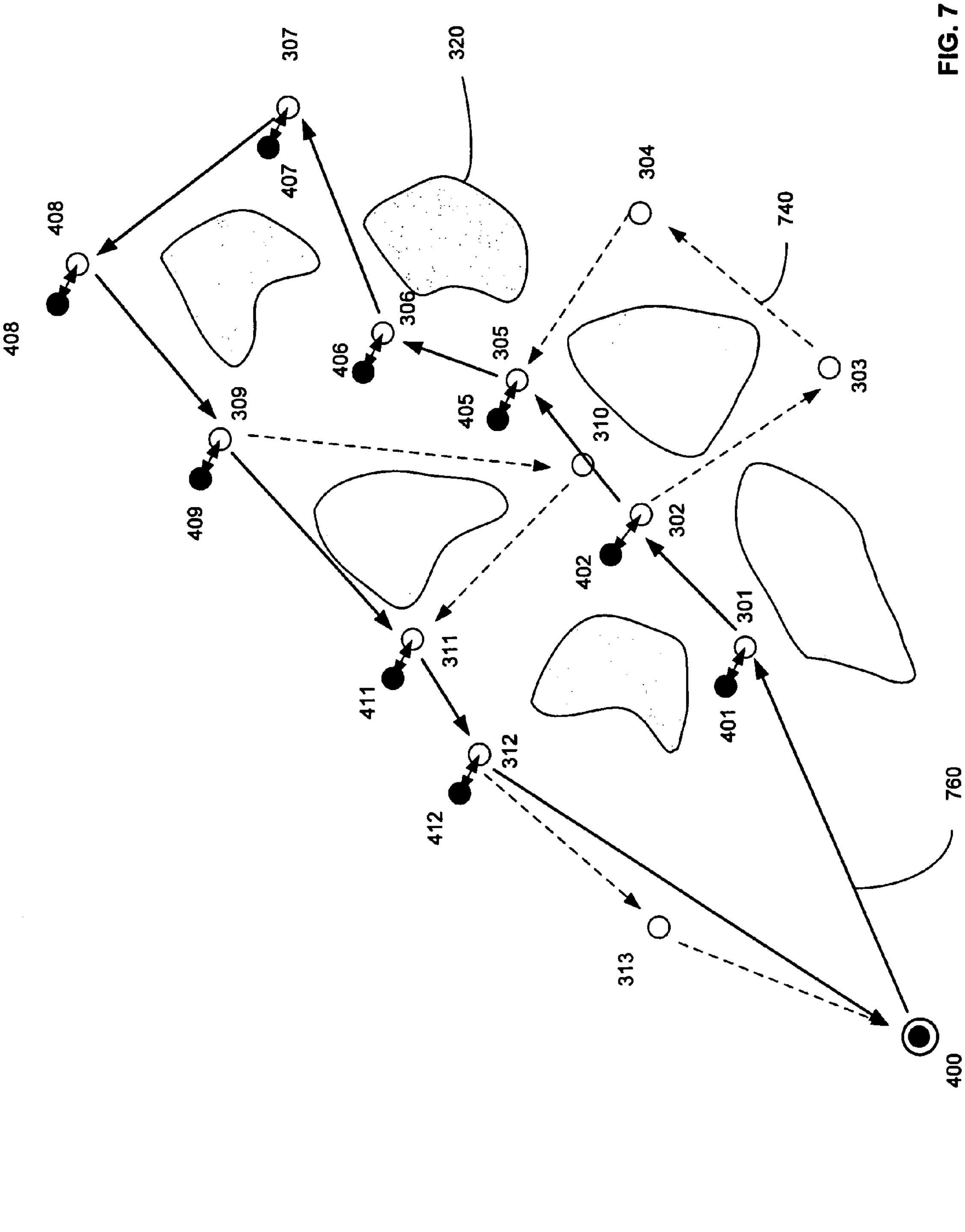
FIG. 7 is a 2-dimensional map with an outline of the optimized path traversal for a radiation delivery source to deliver treatment at a subset of template spatial nodes, in accordance to an embodiment of the invention.

FIG. 7 illustrates a 2D map with an outline of the optimized path traversal for a radiation source to deliver treatment at a partial set of template nodes, in accordance to an embodiment of the invention. FIG. 7 illustrates a similar 2D map as FIGS.

4A and 4B with the exception that the partial set of template nodes where radiation treatment is delivered are connected by a shorter safe path, an optimized path of traversal 760. Similar to FIG. 4B, FIG. 7 illustrates a selected partial set of template nodes, 301-302, 305-309 and 311, 312 where radiation treatment is delivered. The remaining template nodes, 303, 304, 310 and 313, are unused for radiation treatment. Without information provided by direct mapping, the radiation source has to follow path 740 (dashed lines), same as path 440 in FIG. 4B, containing all the template nodes, to ensure a safe course of travel to all the selected partial template nodes to deliver treatment. Like path 440 in FIG. 4B, path 740 consumes a longer time because the radiation source must visit all the unused template nodes even though no radiation treatment is delivered at those positions. With the information generated from direct mapping, once the partial template nodes are identified by the user (e.g., medical physicist, physician etc.,), a shorter path 760 (solid line) can be identified. The shorter optimal path of traversal 760 skips at least one or more unused nodes and includes all the selected partial template nodes where radiation treatment is delivered, while maintaining a path that is collision-free and has no obstruction.

FIG. 7 illustrates one embodiment where all the unused nodes 303, 304, 310, 313 can be skipped and so the optimal path of traversal 760 includes only the partial nodes where radiation treatment is actually delivered. Therefore, the optimal path of traversal 760 essentially illustrates the shortest path of traversal for a new treatment plan. In another embodiment (not illustrated), one or more unused template node may be visited to ensure a collision-free path is obtained while the radiation source visits all the selected partial template nodes to deliver radiation treatment. Furthermore, these one or more unused template nodes that are visited may be visited for one or more times. This embodiment thus illustrates an optimal path of traversal (not shown) that is shorter than the safe or collision-free path defined in an original plan requiring travel to all template nodes, but longer than the shortest path of traversal as illustrated by 760. In either embodiments mentioned above, the object of determining an optimal path of traversal to apply information generated from direct mapping to the partial template nodes identified by the user (medical physicist, physician etc.,) to deliver an equally effective treatment as the original treatment plan using a partial set of template nodes, and traversing these partial set of template nodes while maintaining as short a collision-free path as possible. Therefore, while FIG. 7 illustrates the ideal case of a shortest optimal path of traversal 760 where no unused nodes are visited, in some embodiments, one or more of the unused nodes may be visited and the optimized path of traversal may include more than just the partial template nodes for radiation treatments.

In another embodiment, a reduction to the overall treatment time of an optimal path of traversal can be achieved by re-sequencing of the spatial nodes. Re-sequencing can happen at any time to find a time-optimal sequence. In one embodiment, re-sequencing of the spatial nodes may be performed after the template nodes are determined where radiation treatment is delivered are identified. In another embodiment, re-sequencing can be applied before or after the determination of unused spatial nodes and the skipping of the unused spatial nodes to determine an optimal path of traversal. In yet another embodiment, re-sequencing can also be applied after the optimal path of traversal has been determined using a least number of template nodes for the optimal path of traversal. Still in another embodiment, re-sequencing may be applied after an error occurred when a radiation source travels between two spatial nodes before or after a revised optimal path of traversal is determined. An algorithm is used to evaluate different sequences of spatial nodes, including, but not limited to, template nodes and partial set of template nodes where radiation treatment is delivered, to determine which sequence of spatial nodes can produce the shortest overall time of treatment. One example is where a collision-free path of travel is traversed in reverse order of that specified by planning. Re-sequencing of spatial nodes, like determining which unused nodes can be skipped, takes into account the objective to avoid obstacles. As one of the main objectives, re-sequencing of spatial nodes determines if re-organizing the order in which the spatial nodes are traveled can reduce overall treatment time while maintaining a collision-free path of travel.

The benefits of optimized path of traversal using direct mapping are particularly useful when the radiation source encounters an error unforeseen during a treatment plan when traveling between two spatial nodes. FIG. 8A illustrates a 2D map of a radiation source encountering an error between two spatial nodes while traveling on a safe or collision-free path formed by the template nodes in an original treatment plan, in accordance with an embodiment of the invention. FIG. 8B illustrates a 2D map of a path of travel for a radiation source after resetting upon encountering the error between the two spatial nodes, as formed by the template nodes in an original treatment plan, in accordance with an embodiment of the invention.

FIG. 8A illustrates an embodiment before direct mapping or optimal path traversal has been implemented, where a partial set of template nodes are identified for radiation treatment, but the radiation source still has to travel through all the template nodes to ensure a safe or collision-free path of travel as defined in an original treatment plan. As shown, radiation source travels along a safe or collision-free path of travel 840 that includes all template nodes to deliver radiation treatments at the partial template nodes. When traveling between node 311 to 312, after delivering radiation treatment in an orientation 411 (as explained earlier), the radiation source encountered an error 860 en route to template node 312. This error may be a software error or a physical error, for example, as an illustration but not a restriction, an object was accidentally placed in the path, or alternately, the radiation source fails to return to a particular orientation suitable for traveling between nodes. Upon encountering the error, the radiation source resets itself to the home position 300.

FIG. 8B illustrates an embodiment before direct mapping or optimal path traversal has been implemented, where the radiation source completes the treatment plan after resetting itself upon encountering an error. In fact, radiation source travels along the exact same path of travel 840 as previously illustrated in FIG. 8A, only not to deliver radiation treatments at the selected partial template nodes where radiation treatments were delivered before the error occurred. For example, since radiation treatments were delivered at 401-402, 405, 406-409 and 411 (or the corresponding 301-302, 305, 306-309 and 311, as explained earlier), no radiation treatment will be delivered at those nodes. As the radiation source travels to node 311, it continues along the same path as before to node 312, to deliver radiation treatment at the designated partial template node(s) previously unvisited before the error occurred to complete the treatment plan. Therefore, without direct mapping to determine an optimal path traversal, the safe or collision-free path of travel for the radiation source is rigid, fixed and un-adjustable even when an error occurs. The user is expected to solve the problem whether it is software related, mechanical related, if a physical object was obstructing the radiation source or any other problem that may have caused the error.

With direct mapping or optimal path traversal, radiation source travel path becomes flexible and can be re-calculated to reduce overall treatment time by finding a path of travel that is safe and as short as possible by skipping one or more template nodes previously visited before the error occurrence. FIG. 9A illustrates a 2D map of a radiation source encountering an error between two nodes while traveling on an optimized path of traversal determined from direct mapping, in accordance with an embodiment of the invention. FIG. 9B illustrates a 2D map of a new optimized safe path determined by direct mapping after resetting upon encountering the error between the two spatial nodes, in accordance with an embodiment of the invention.

FIG. 9A illustrates an embodiment after direct mapping or optimal path traversal has been implemented, where a radiation source travels on a shortest yet safe path 960 to deliver radiation treatments at only the partial template nodes as identified. For purposes of illustration, while the radiation source travels along a much shorter path 960 as compared to 840 in FIG. 8A, the radiation source also encounters an error after delivering radiation treatment at node 411 (or 311). The radiation source responds by resetting itself to the home position 300. In one embodiment, a new safe path 970 is identified based on the information gathered from the direct mapping, the information about the all template nodes that the radiation source visited (e.g., 301-311), the last node where the radiation delivered treatment (e.g., 311), the next unvisited node before the error occurred (e.g., 312), and the next partial template node (e.g., 312) where the radiation source has to deliver radiation treatment(s). Based on the aforementioned information, the system will identify an optimal path of traversal that is safe and as short as possible from home position to the next unvisited partial template node where radiation source has to deliver treatment. This optimal path of traversal will be identified by determining which of the previously visited nodes, before the error occurred on the previous travel path, can be skipped before reaching the next unvisited partial template node where radiation treatment is to be delivered. Often at least one or more of the previously visited template nodes on the initial safe path of travel can be skipped. In another embodiment, a new safe path may be identified from information about the last visited template node (e.g., 311) before the error and the next unvisited node (e.g., 312) before the error.

FIG. 9B illustrates an embodiment after direct mapping or optimal path traversal has been implemented, where a radiation source travels on a re-calculated path, a shortest yet safe path 970, from the home position to reach the next unvisited partial template node where radiation treatment is expected according to the treatment plan before the error occurrence. In one embodiment, the radiation source is able to move directly from the home position 300 to the next unvisited template node 312 (or 412) where radiation treatment is to be delivered according to the treatment plan along path 970. In this embodiment, the radiation source can move directly from home to the next unvisited partial template node selected for radiation treatment, however, in other embodiments, one or more previously visited template nodes before the error may be visited first in establishing the shortest safe path (not illustrated). In an embodiment, after an error, only the path from the home position 300, after the radiation source resets, to the next unvisited partial template node selected for radiation treatment, is recalculated to minimize travel time. Since the original path was already planned using the information based on direct mapping, the original path is supposed to be the shortest and safest. Therefore the path of travel from the next unvisited partial template node selected for radiation treatment before the error to the last node in order to complete the treatment plan before returning to the home position 300 will remain same. In other words, upon encountering an error, only the portion of the path from the reset home position 300 to the next unvisited partial template node selected for radiation treatment is re-defined or re-calculated, but the rest of the travel path from that point onward to complete the treatment plan remains unchanged.

Figure 10:
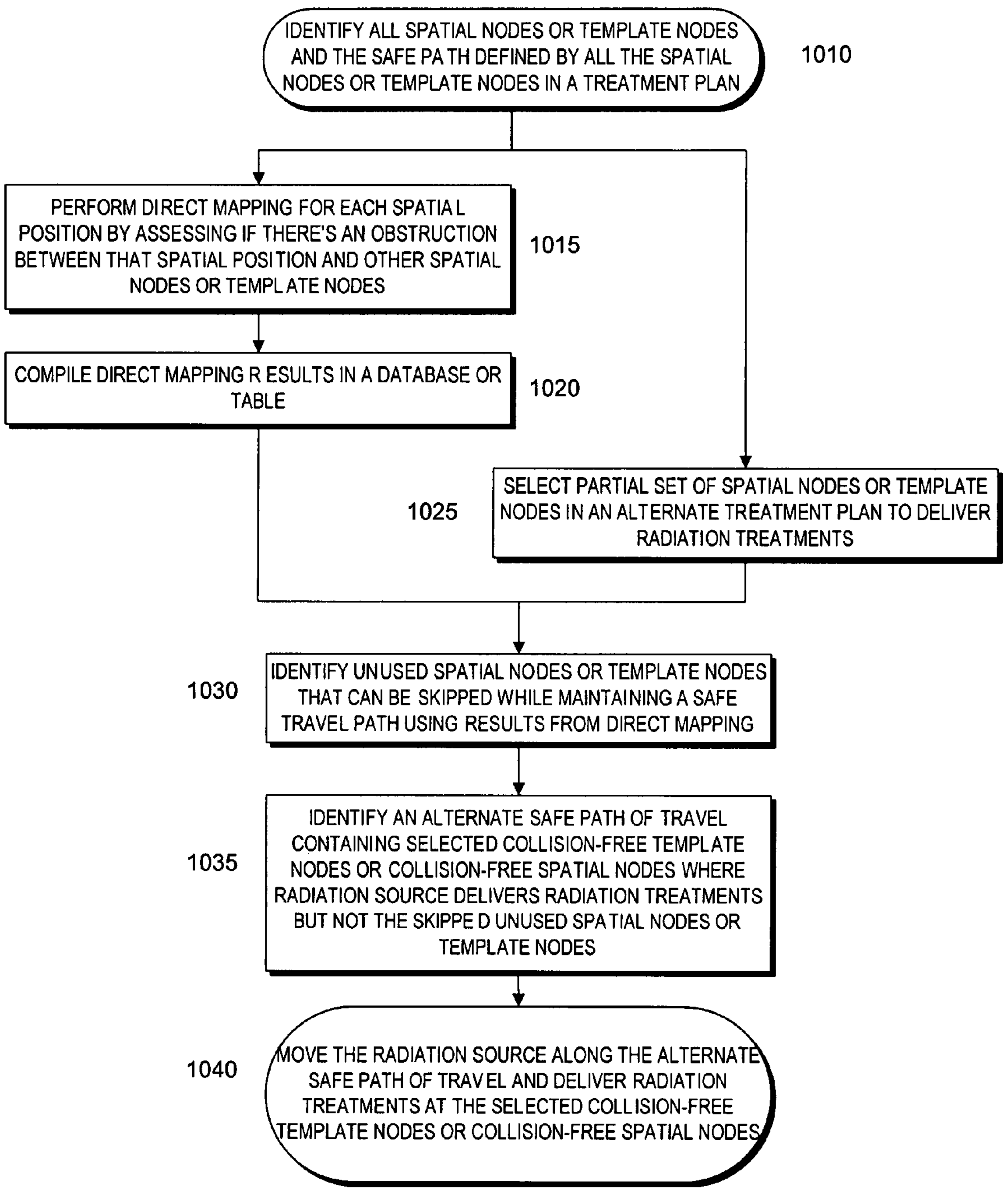
FIG. 10 is a flow chart illustrating a process for determining an optimized safe or collision-free path of travel for a radiation delivery source to determine and implement an optimized path traversal for a subset of template spatial nodes, in accordance with an embodiment of the invention.

FIG. 10 is a flow chart illustrating a process for determining an optimized safe path of travel for a radiation source to deliver radiation treatments at selected partial template nodes without following a safe or collision-free plan of travel that includes all template nodes, in accordance with an embodiment of the invention. All template nodes and the safe or collision-free path defined by all template nodes in a treatment plan must be identified in step 1010 before determining the optimized safe path of travel. This step is the same as selecting template nodes from a superset of nodes as described earlier in this disclosure. After the template nodes and the safe or collision-free path that includes all the template nodes are determined, steps 1015 and 1020 are performed in parallel with step 1025. In step 1015, the system performs direct mapping for each spatial position by assessing if there is an obstruction between that spatial position, defined by the home position or any of the template nodes, and each of the template nodes. This step is same as generation of the information as illustrated earlier in FIGS. 5A-5D. In step 1020, the system compiles the information generated by direct mapping into a database or table that allows easy access for implementation before or during treatment planning and/or before or during treatment plan execution. While steps 1015 and 1020 are being performed, a partial set of template nodes are selected in an alternate treatment plan to deliver radiation treatments. This alternate treatment plan, equally effective as the original treatment plan, is defined by delivering radiation treatment at less number of template nodes than originally defined. After steps 1020 and 1025 are completed, step 1030 is to identify unused template nodes that can be skipped while maintaining a safe or collision-free travel path using results generated from direct mapping. Once the number of unused nodes that can be skipped is identified, step 1035 is to identify the alternate safe or collision-free path of travel containing selected template nodes where radiation source delivers radiation treatments but skipping the unused template nodes. Ideally, a shortest yet safe path of travel that enables the radiations source to visit all the selected partial template nodes where radiation treatment is delivered is determined. The last step 1040 is to move the radiation source along the alternate safe path of travel and to deliver radiation treatments at the selected template nodes according to the alternate treatment plan. The object is to achieve a level of therapeutic effectiveness that is equivalent to the original treatment plan while completing the treatment is a shorter time.

Figure 11:
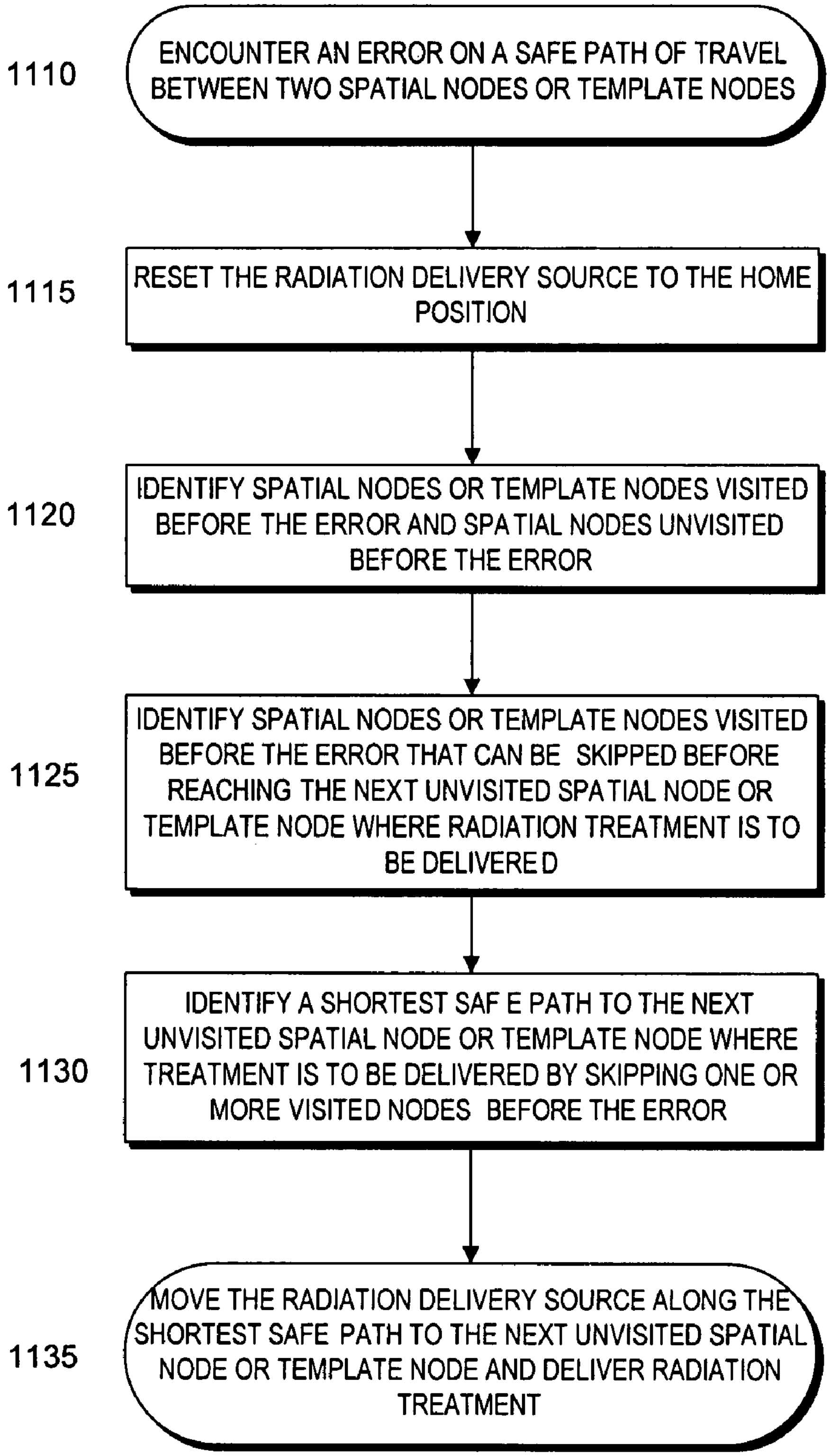
FIG. 11 is a flow chart illustrating a process to determine a modified safe or collision-free path of travel after a radiation delivery source encounters an error while traveling between two spatial nodes, in accordance with an embodiment of the invention.

FIG. 11 is a flow chart illustrating a process for determining an alternate safe or collision-free path for the radiation source to travel to the next unvisited selected template node to deliver radiation treatment after encountering an error without having to revisit all the template nodes previously visited before the error occurrence, in accordance to an embodiment of the invention. Step 1110 begins with the radiation source encountering an error on a safe or collision-free path of travel between two template nodes. The safe or collision-free path of travel is often shorter than the safe or collision-free path of travel defined by all the template nodes, but in some cases, the safe or collision-free path of travel can be defined by all the template nodes if a shorter yet safe path is not identified. After encountering an error, step 1115 resets the radiation source to the home position so a new plan of travel can be identified. Step 1120 identifies all the template nodes visited prior to the error occurrence and all the partial selected template nodes unvisited before the error where radiation treatment is to be delivered. Once both the visited template nodes and the unvisited template nodes are identified, the system can go back to the information generated from direct mapping and in step 1125 identify the template nodes visited before the error that can be skipped before reaching the next unvisited template node where radiation treatment is to be delivered. Once one or more previously visited template nodes that can be skipped are identified, in step 1130, the system identifies a shortest safe or collision-free path to the next unvisited partial template node where treatment is to be delivered by skipping the one or more visited template node before the error occurred. In the last step 1135, the system moves the radiation source along the shortest safe or collision-free path to the next unvisited template node and delivers radiation treatment to the remainder of the unvisited partial template nodes to complete the treatment plan. Note that only the path from the home position to the next unvisited partial template node before the error occurred is modified because the goal is to reach the next unvisited partial template node where radiation treatment is delivered in a shortest yet safe or collision-free path. The travel plan from the next unvisited partial template node until the last unvisited partial template node is not changed and remains the same as before the error occurrence.

One should appreciate that the direct mapping process and the determination of an optimal path traversal can be used in conjunction with the determination of an optimized treatment plan as described in co-pending U.S. Published Patent Application No. 2007/0071168 titled "Workspace Optimization for Radiation Treatment Delivery System," filed on Sep. 28, 2005. For instance, in one embodiment, a user (e.g., medical physicist, physician etc.,) utilizes the treatment planning software to generate a treatment plan, using all the template nodes that are available to the system, to meet the min/max dose prescription constraints. Accordingly, a treatment plan using all the template nodes may represent the highest quality treatment plan attainable by radiation treatment delivery system. The user also identifies a different treatment plan, equally effective as the first treatment plan delivering radiation treatments at all template nodes, to treat a target using a fewer number, or subset, of the template nodes. An equally effective treatment plan that can be delivered using a fewer number of nodes will save treatment delivery time due to the fewer number of nodes that have to be traversed by system during treatment delivery. Typically, a database is searched to determine whether any template node subsets exist that may be possible alternatives to all template nodes used. The database may store template node subset indexed to anatomy features (e.g., spinal lesions, prostate lesions, breast lesions, lung lesions, etc.). The database may also be searched based on whether other treatment plan parameters may be optimized such as total number of imaging centers, total number of couch positions, total number of SADs, etc. If the preliminary search/analysis of the database suggests that one or more of the template node subsets may be possible alternatives to the complete template node set, then treatment plan developed using the template node subset is evaluated to see whether it is of sufficient quality. The choice whether to use the template node subset treatment plan or the complete template node treatment plan may be made by the medical physicist or radiation oncologist, the operator of the radiation treatment delivery system, or even by software according to defined rules. The choice whether to a template node subset treatment plan or the complete template node treatment plan may require balancing the projected times savings versus the quality deviation. If the treatment time savings are substantial and the quality deviation is small, then the template node subset treatment plan may be selected for treatment delivery. The methods and apparatus described herein may be used to further reduce the treatment delivery time by further reducing the number of nodes that are traveled to in delivering the template node subset treatment plan.

Figure 12:
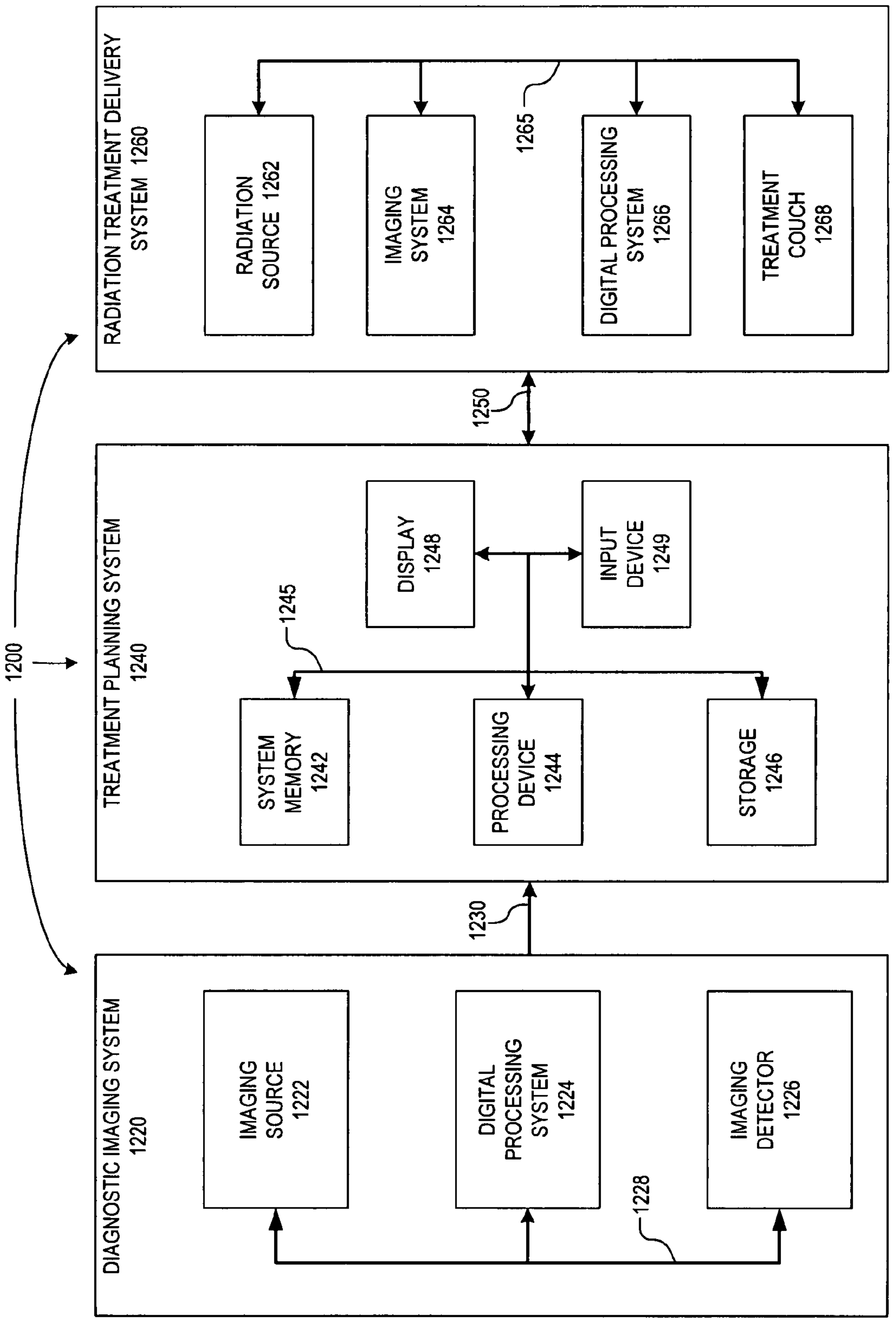
FIG. 12 is a block diagram illustrating a patient treatment system for generating diagnostic images, generating a treatment plan, and delivering the treatment plan in accordance with an embodiment of the invention.

The method and apparatus for determining an optimized path of traversal for a radiation source may be combined with a patient treatment system or function as part of the radiation treatment system. FIG. 12 is a block diagram illustrating a patient treatment system 1200 for generating diagnostic images, generating a treatment plan, and delivering the treatment plan to a patient, in which features of the present invention may be implemented. As described below and illustrated in FIG. 12, system 1200 may include a diagnostic imaging system 1220, a treatment planning system 12400 and a radiation treatment delivery system 1260. It should be noted that FIG. 12 merely illustrates an example of a patient treatment system, other alternative embodiments are possible.

Diagnostic imaging system 1220 may be any system capable of producing medical diagnostic images of a volume of interest ("VOI") in a patient that may be used for subsequent medical diagnosis, treatment planning and/or treatment delivery. For example, diagnostic imaging system 1220 may be a computed tomography ("CT") system, a magnetic resonance imaging ("MRI") system, a positron emission tomography ("PET") system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1220 includes an imaging source 1222 to generate an imaging beam (e.g., x-rays, ultrasonic waves, radio frequency waves, etc.) and an imaging detector 1226 to detect and receive the beam generated by imaging source 1222, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 1222 and the imaging detector 1226 are coupled to a digital processing system 1224 to control the imaging operation and process image data. Diagnostic imaging system 1220 includes a bus or other means 1228 for transferring data and commands among digital processing system 1224, imaging source 1222 and imaging detector 1226. Digital processing system 1224 may include one or more general-purpose processors (e.g., a microprocessor), special purpose processor such as a digital signal processor ("DSP") or other type of device such as a controller or field programmable gate array ("FPGA"). Digital processing system 1224 may also include other components (not shown)

such as memory, storage devices, network adapters and the like. Digital processing system 1224 may be configured to generate digital diagnostic images in a standard format, such as the DICOM (Digital Imaging and Communications in Medicine) format, for example. In other embodiments, digital processing system 1224 may generate other standard or non-standard digital image formats. Digital processing system 1224 may transmit diagnostic image files (e.g., the aforementioned DICOM formatted files) to treatment planning system 1240 over a data link 1230, which may be, for example, a direct link, a local area network ("LAN") link or a wide area network ("WAN") link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 1200 includes a processing device 1244 to receive and process image data. Processing device 1244 may represent one or more general-purpose processors (e.g., a microprocessor), special purpose processor such as a DSP or other type of device such as a controller or FPGA. Processing device 1244 may be configured to execute instructions for performing treatment planning operations discussed herein.

Treatment planning system 1240 may also include system memory 2020 that may include a random access memory ("RAM"), or other dynamic storage devices, coupled to processing device 1244 by bus 1245, for storing information and instructions to be executed by processing device 1244. System memory 1242 also may be used for storing temporary variables or other intermediate information during execution of instructions by processing device 1244. System memory 1242 may also include a read only memory ("ROM") and/or other static storage device coupled to bus 1245 for storing static information and instructions for processing device 1244.

Treatment planning system 1240 may also include storage device 1246, representing one or more storage devices (e.g., a magnetic disk drive or optical disk drive) coupled to bus 1245 for storing information and instructions. Storage device 1246 may be used for storing instructions for performing the treatment planning steps discussed herein.

Processing device 1244 may also be coupled to a display device 1248, such as a cathode ray tube ("CRT") or liquid crystal display ("LCD"), for displaying information (e.g., a 2D or 3D representation of the VOI) to the user. An input device 1249, such as a keyboard, may be coupled to processing device 1244 for communicating information and/or command selections to processing device 1244. One or more other user input devices (e.g., a mouse, a trackball or cursor direction keys) may also be used to communicate directional information, to select commands for processing device 1244 and to control cursor movements on display 1248.

It will be appreciated that treatment planning system 1240 represents only one example of a treatment planning system, which may have many different configurations and architectures, which may include more components or fewer components than treatment planning system 1240 and which may be employed with the present invention. For example, some systems often have multiple buses, such as a peripheral bus, a dedicated cache bus, etc. The treatment planning system 1240 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 1240 may share its database (e.g., data stored in storage device 1246) with a treatment delivery system, such as radiation treatment delivery system 1260, so that it may not be necessary to export from the treatment planning system prior to treatment delivery. Treatment planning system 1240 may be linked to radiation treatment delivery system 1260 via a data link 1250, which may be a direct link, a LAN link or a WAN link as discussed above with respect to data link 1250. It should be noted that when data links 1250 and 1230 are implemented as LAN or WAN connections, any of diagnostic imaging system 1320, treatment planning system 1240 and/or radiation treatment delivery system 1260 may be in decentralized locations such that the systems may be physically remote from each other. Alternatively, any of diagnostic imaging system 1220, treatment planning system 1240 and/or radiation treatment delivery system 1260 may be integrated with each other in one or more systems.

Radiation treatment delivery system 1260 includes a therapeutic and/or surgical radiation source 1262 to administer a prescribed radiation dose to a target volume in conformance with a treatment plan. Radiation treatment delivery system 1260 may also include an imaging system 1264 (including imaging sources 1222 and detectors 1226) to capture intra-treatment images of a patient volume (including the target volume) for registration or correlation with the diagnostic images described above in order to position the patient with respect to the radiation source. Radiation treatment delivery system 1260 may also include a digital processing system 1266 to control therapeutic radiation source 1262, imaging system 1264, and a patient support device such as a treatment couch 1268. Digital processing system 1266 may include one or more general-purpose processors (e.g., a microprocessor), special purpose processor such as a DSP or other type of device such as a controller or FPGA. Digital processing system 1266 may also include other components (not shown) such as memory, storage devices, network adapters and the like. Digital processing system 1266 may be coupled to therapeutic radiation source 1262, imaging system 1264 and treatment couch 1268 by a bus 1265 or other type of control and communication interface.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, wields in the construction industry and drill cores in the petroleum industry) and seismic surveying. In such applications, for example, "treatment" may refer generally to the application of radiation beam(s).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method, comprising:

providing a plurality of spatial nodes used in a treatment plan, wherein the plurality of spatial nodes is a partial set selected from a superset of all possible spatial nodes, each of the plurality of spatial nodes representing a position of a radiation source made available to the treatment plan for delivering radiation to a target;

identifying a number of unused spatial nodes, from among the plurality of spatial nodes, at which radiation is not delivered according to the treatment plan; and skipping travel to one or more of the unused nodes by the radiation source when administering the treatment plan.

2. The method of claim 1 further comprising determining a collision-free path of travel for the radiation source that does not contain an obstruction between any two consecutive spatial nodes according to the treatment plan.

3. The method of claim 1 further comprising determining a collision-free path of travel for the radiation source that contains no obstruction, by skipping the one or more of the unused spatial nodes.

4. The method of claim 3 further comprising moving the radiation source along the collision-free path of travel that does not contain an obstruction between any two consecutive spatial nodes in the administering of the treatment plan after the skipping travel to one or more of the unused nodes by the radiation source.

5. The method of claim 3 further comprising moving the radiation source according to the collision-free path of travel to deliver radiation treatments at a number of selected spatial nodes.

6. The method of claim 3 wherein the determining of a collision-free path of travel for the radiation source is based upon at least one of a look-up table or a reference database that is generated from an off-line simulation.

7. The method of claim 3, further comprising moving the radiation source according to treatment plan where the radiation source skips one or more unused spatial nodes and travels in a shorter path defined by a path without the one or more unused spatial nodes relative to a path with the one or more unused spatial nodes.

8. The method of claim 1 wherein the plurality of spatial nodes is ordered in sequence from a lowest sequenced spatial node to a highest sequenced spatial node.

9. The method of claim 8 wherein the treatment plan begins from the home position to the lowest sequenced spatial node and terminates at the home position after the highest sequenced spatial node.

10. The method of claim 1 wherein the one or more unused nodes is skipped if a path of travel between a spatial node before and a spatial node after the one or more unused nodes has no obstruction.

11. The method of 1 wherein the radiation source is coupled to a robotic arm having 5 or more degrees of freedom.

12. An apparatus, comprising:

means for providing a plurality of spatial nodes used in a treatment plan, wherein the plurality of spatial nodes is a partial set selected from a superset of all possible spatial nodes, each of the plurality of spatial nodes representing a position of a radiation source made available to the treatment plan for delivering radiation; and means for skipping travel to a number of unused spatial nodes, from among the plurality of spatial nodes, where radiation is not delivered according to the treatment plan, while maintaining a collision-free path of travel for the radiation source that has no obstruction.

13. The apparatus of claim 12 wherein an original path of travel further comprises the plurality of spatial nodes wherein each of the spatial node in the plurality of spatial nodes is visited in an order defined by the treatment plan to travel along a path that is obstruction-free.

14. The apparatus of claim 12 wherein the radiation source delivers radiation treatments at a set of useable spatial nodes in the plurality of spatial nodes that prescribes an equally effective dose to a target as if the radiation source delivers treatment at each of the spatial node in the plurality of spatial nodes in the treatment plan.

15. The apparatus of claim 12 wherein the plurality of spatial nodes is ordered in sequence from a lowest sequenced spatial node to a highest sequenced spatial node.

16. The apparatus of claim 12 wherein the collision-free path of travel and the original path of travel follows an order that begins with the lowest sequenced spatial node and terminates after the highest sequenced spatial node.

17. The apparatus of claim 12 wherein the radiation source is coupled to a robotic arm having 5 or more degrees of freedom.

18. The apparatus of claim 17 wherein the robotic arm has 6 degrees of freedom comprising 5 rotational degrees of freedom and 1 substantially vertical, linear degree of freedom.

19. A system, comprising:

a radiation source;

a processor coupled to the radiation source, the processor is configured to determine if travel paths between each of a plurality of spatial nodes and rest of the plurality of spatial nodes has an obstruction, each of the plurality of spatial nodes representing a position in space in which the radiation source can occupy in a workspace, wherein the plurality of spatial nodes is a partial set selected from a superset of all possible spatial nodes;

the processor is further configured to determine one or more of unused spatial nodes in the plurality of spatial nodes that can be skipped to reduce time to complete a path of travel where the radiation source delivers treatment at a number of used spatial nodes in the plurality of spatial nodes; and the processor is further configured to determine a new travel plan for the radiation source by skipping the one or more of the unused spatial nodes; and a database coupled to the processor, the database is configured to store, information about the travel paths, the one or more of unused spatial nodes that can be skipped, and the new travel plan for the radiation source.

20. A machine-accessible medium that provides instructions that, if executed by a machine, will cause the machine to perform operations, comprising:

providing a plurality of spatial nodes used in a treatment plan, wherein the plurality of spatial nodes is a partial set selected from a superset of all possible spatial nodes, each of the plurality of spatial nodes representing a position of a radiation source made available to the treatment plan for delivering radiation to a target;

identifying a number of unused spatial nodes, from among the plurality of spatial nodes, at which radiation is not delivered according to the treatment plan; and skipping travel to one or more of the unused nodes by the radiation source when administering the treatment plan.

21. The machine-accessible medium of claim 20, further providing instructions that, if executed by the machine, will cause the machine to perform further operations, comprising:

determining a collision-free path of travel for the radiation source that does not contain an obstruction between any two consecutive spatial nodes according to the treatment plan.

22. The machine-accessible medium of claim 20, further providing instructions that, if executed by the machine, will cause the machine to perform further operations, comprising:

determining a collision-free path of travel for the radiation source that contains no obstruction, by skipping the one or more of the unused spatial nodes.

23. The machine-accessible medium of claim 22, wherein the determining of a collision-free path of travel for the radiation source is based upon at least one of a look-up table or a reference database that is generated from an off-line simulation.

24. The machine-accessible medium of claim 22, further providing instructions that, if executed by the machine, will cause the machine to perform further operations, comprising:

moving the radiation source according to the collision-free path of travel to deliver radiation treatments at a number of selected spatial nodes.

25. The machine-accessible medium of claim 20, wherein the plurality of spatial nodes is ordered in sequence from a lowest sequenced spatial node to a highest sequenced spatial node.

26. The machine-accessible medium of claim 20, wherein the one or more unused nodes is skipped if a path of travel between a spatial node before and a spatial node after the one or more unused nodes has no obstruction.

27. The machine-accessible medium of claim 20, wherein the radiation source is coupled to a robotic arm having 5 or more degrees of freedom.

* * * * *